United States Patent
Haque et al.

(10) Patent No.: US 9,745,549 B2
(45) Date of Patent: Aug. 29, 2017

(54) CELL CULTURE SUBSTRATE, AND CELL CULTURING METHOD USING THE SUBSTRATE AND METHOD FOR INDUCING DIFFERENTIATION OF PLURIPOTENT STEM CELLS USING THE SUBSTRATE

(71) Applicants: SOMAR Corp., Tokyo (JP); Toshihiro Akaike, Tokyo (JP)

(72) Inventors: Amranul Haque, Yokohama (JP); Masato Nagaoka, Brookfield, WI (US); Toshihiro Akaike, Tokyo (JP)

(73) Assignees: SOMAR CORP., Tokyo (JP); Toshihiro Akaike, Tokyo (JP)

( * ) Notice: Subject to any disclaimer, the term of this patent is extended or adjusted under 35 U.S.C. 154(b) by 0 days.

(21) Appl. No.: 13/865,642

(22) Filed: Apr. 18, 2013

(65) Prior Publication Data

US 2014/0113372 A1    Apr. 24, 2014

(30) Foreign Application Priority Data

Oct. 19, 2012   (JP) ................. 2012-232339

(51) Int. Cl.
| | |
|---|---|
| *A61K 38/00* | (2006.01) |
| *C12N 5/0797* | (2010.01) |
| *C12N 5/079* | (2010.01) |
| *C12N 5/0735* | (2010.01) |
| *C12N 5/074* | (2010.01) |

(52) U.S. Cl.
CPC ......... *C12N 5/0623* (2013.01); *C12N 5/0606* (2013.01); *C12N 5/0618* (2013.01); *C12N 5/0696* (2013.01); *C12N 2506/02* (2013.01); *C12N 2506/45* (2013.01); *C12N 2533/30* (2013.01); *C12N 2533/50* (2013.01)

(58) Field of Classification Search
None
See application file for complete search history.

(56) References Cited

U.S. PATENT DOCUMENTS

| | | | |
|---|---|---|---|
| 2005/0002919 A1 | 1/2005 | Brenner et al. | |
| 2007/0155013 A1* | 7/2007 | Akaike ............... | C12N 5/0606 435/354 |
| 2008/0274950 A1* | 11/2008 | Kilshaw et al. ........ | 514/8 |
| 2012/0207744 A1 | 8/2012 | Mendlein et al. | |

FOREIGN PATENT DOCUMENTS

| | | |
|---|---|---|
| JP | 2010-63411 A | 3/2010 |
| WO | WO 01/51616 A2 | 7/2001 |
| WO | WO 03/020920 A1 | 3/2003 |
| WO | WO 2007/069666 A1 | 6/2007 |
| WO | WO 2009/057831 A1 | 5/2009 |
| WO | WO 2009/075119 A1 | 6/2009 |

OTHER PUBLICATIONS

Halbleib et al, Cadherins in development: cell adhesion, sorting, and tissue morphogenesis, Genes Dev. 2006 20: 3199-3214.*
Bard et al, A Molecular Clutch between the Actin Flow and N-Cadherin Adhesions Drives Growth Cone Migration, The Journal of Neuroscience, Jun. 4, 2008 • 28(23):5879-5890.*
Utton et al, Soluble N-cadherin stimulates fibroblast growth factor receptor dependent neurite outgrowth and N-cadherin and the fibroblast growth factor receptor co-cluster in cells, Journal of Neurochemistry, 2001, 76, 1421-1430.*
Ozawa (The Journal of Biological Chemistry vol. 277, No. 22, Issue of May 31, pp. 19600-19608, 2002).*
Straub et al (J. Cell Biol. vol. 195 No. 5 873-887), 2011.*
Yue et al. (Biomaterials 31 (2010) 5287-5296).*
Haque et al., "Characterization and neural differentiation of mouse embryonic and induced pluripotent stem cells on cadherin-based substra", Biomaterials 33, pp. 5094-5106, (2012).
Hogan et al. "Manipulating the Mouse Embryo: A Laboratory Manural, Second Edition", Cold Spring Harbor Labortory Press, 1994.
Amit et al., "Feeder Layer- and Serum-Free Culture of Human Embryonic Stem Cells", Biology of Reproduction, vol. 70 (2004) pp. 837-845.
Lakshmipathy et al., "Efficient Transfection of Embryonic and Adult Stem Cells", Stem Cells, vol. 22 (2004) pp. 531-543.
Nagaoka et al., "Immobilized E-cadherin model can enhance cell attachment and differentiation of primary hepatocytes but not proliferation", Biotechnology Letters, vol. 24 (2002) pp. 1857-1862.
Nagaoka et al., "Single amino acid substitution in the mouse IgG1 Fc region induces drastic enhancement of the affinity to protein A", Protein Engineering, vol. 16, No. 4 (2003) pp. 243-245.
Sato et al., "Maintenance of pluripotency in human and mouse embryonic stem cells through activation of Wnt signaling by a pharmacological GSK-3-specific inhibitor", Nature Medicine, vol. 10, No. 1 (2004) pp. 55-63.
Turksen, "Embryonic Stem Cells: Methods and Protocols", Methods in Molecular Biology, vol. 185, Humana Press Inc., 2002.
Xu et al., "Feeder-free growth of undifferentiated human embryonic stem cells", Natura Biotechnology, vol. 19 (2001) pp. 971-974.

(Continued)

*Primary Examiner* — James H Alstrum Acevedo
*Assistant Examiner* — Sergio Coffa
(74) *Attorney, Agent, or Firm* — Birch, Stewart, Kolasch & Birch, LLP

(57) ABSTRACT

[Problem] To provide a cell culture substrate, and a cell culturing method using the substrate and a method for inducing differentiation of pluripotent stem cells using the substrate, which allow culturing of pluripotent stem cells and allow differentiation of pluripotent stem cells into a specified cell species, particularly neural and neural progenitor cells, at a high purity.

[Means for Solution] A cell culture substrate, characterized in that, onto the surface, one or more selected from the group consisting of N-cadherin, a fusion protein comprising an entire or partial region of N-cadherin, and a fusion protein comprising an entire or partial region of a protein homologous to N-cadherin are immobilized or coated.

15 Claims, 8 Drawing Sheets

(56) References Cited

OTHER PUBLICATIONS

Australian Office Action for Appl. No. 2013204932 dated Jul. 3, 2014.
Yue, X.S. et al, "A fusion protein N-cadherin-Fc as an artificial extracellular matrix surface for maintenance of stem cell features," Biomaterials, 2010, vol. 31, pp. 5287-5296.
Japanese Office Action, dated Aug. 2, 2016, for Japanese Application No. 2012-232339.
Yue et al., "Regulation of Neurodifferentiation of mES cells on N-cadherin Chimeric Protein," Regenerative Therapy, vol. 10 Suppl., Feb. 1, 2011, p. 147, with English translation.

* cited by examiner

SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaggaagcat cgaattctgg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagttatgga gcggagcagc                                              20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagtcttacc gaaggatgtg c                                            21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atcagctctc gatccagagg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctcggatct ctggtcaagt                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tacagagccg gcagtcatac                                              20

```
<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaacgccttc atggtatgg                                                  19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agccgttcat gtaggtctgc                                                 20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctacataca ggactctgct g                                               21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaactctaga ctcactggat tct                                             23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11 cgatccccett ttctcctttc                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgcagcaacc taacaagtgg                                                 20
```

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcagacttcc accgagcag                                                19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aggggaaaga tcatggccc                                                19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggtaagacc cgagttcctc                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atcaccactt tgccaccttc                                               20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agcgatgagc acggcatag                                                19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caggttccaa gtccaccaga                                               20

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggagagggac aactttgcac                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gctctaggga ctcgttcgtg                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgcccttcca tctttgcttg                                              20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tctgcccgtt caacatcctt ag                                           22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcctgcactc ccgctcagag                                              20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccaagagcag cccatcaaag g                                            21

<210> SEQ ID NO 25
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgccaaaga aagaaacgac                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agaggctgta gaacaggatt                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgctgccct acatgaacgt                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagtcctggg cctgtacatt                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tattggctgc agctaagcgg                                                 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gactcggact caggtgaggt                                                 20

<210> SEQ ID NO 31
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tttgtgtata agcccgagat gg                                              22

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aagattgaga aaacacgcat gac                                             23

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
accttatggc gtagaaatgc tgagggtg                                        28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctgaatactt gaggtcactg ttctcggg                                        28

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caccatcagg ttccacagg                                                  19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttgaggcagg gtagagtgc                                                  19

<210> SEQ ID NO 37
<211> LENGTH: 21
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 37
cctaaggcca accgtgaaaa g                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcttcatggt gctaggagcc a                                              21
```

CELL CULTURE SUBSTRATE, AND CELL CULTURING METHOD USING THE SUBSTRATE AND METHOD FOR INDUCING DIFFERENTIATION OF PLURIPOTENT STEM CELLS USING THE SUBSTRATE

SEQUENCE LISTING

The instant application contains a Sequence Listing which has been submitted in ASCII format via EFS-Web and is hereby incorporated by reference in its entirety. Said ASCII copy, created on Sep. 3, 2013, is named 2114-0161PUS1_SL.txt and is 9,024 bytes in size.

TECHNICAL FIELD

The present invention relates to a cell culture substrate, and a cell culturing method using the substrate and a method for inducing differentiation of pluripotent stem cells using the substrate, and specifically to a cell culture substrate, and a cell culturing method using the substrate and a method for inducing differentiation of pluripotent stem cells using the substrate, which allow culturing of pluripotent stem cells and allow differentiation of pluripotent stem cells into a specified cell species at a high purity.

BACKGROUND ART

In order to continue to live, organisms have the ability to rapidly replace and repair lost or damaged cells and tissue, and this ability is known as "regenerative capacity". Examples of "regenerative capacity" in higher animals include the commonly known phenomena of wound healing of skin and blood vessels, but even parenchymal organs such as the liver and kidneys are known to undergo cell growth and tissue reconstruction for rapid restoration of tissue homeostasis in response to tissue damage. Recent years have seen attempts to utilize this innate "regenerative capacity" of biological organisms to achieve cures or amelioration of various diseases and wounds, and such new medical techniques are coming to be known as "regenerative medicine".

Stem cells play a central role in practicing "regenerative medicine". "Stem cells" can be generally defined as undifferentiated cells having the ability to differentiate into specialized cells or polyfunctional cells, as well as having the ability to self-replicate, allowing repeated generation of cells identical to themselves. Unique stem cells are found in each tissue and cell type, and for example, blood cells such as erythrocytes, lymphocytes and megakaryocytes are produced via progenitor cells derived from stem cells known as "hematopoietic stem cells", while skeletal muscle cells are produced from stem cells/precursor cells known as "satellite cells" and "myoblasts". Additional types that have been identified to date include neural stem cells that are found in neural tissue such as the brain and spinal cord and produce neurons and glial cells, epidermal stem cells that produce epidermal cells and hair follicle cells, oval cells (hepatic stem cells) that produce hepatocytes and bile duct cells, and cardiac stem cells that produce cardiomyocytes.

Some regenerative medicine treatments using stem cells or precursor cells derived from such cells have already been implemented, and infusion graft methods with hematopoietic stem cells or hematopoietic precursor cells are well known for treatment of conditions caused by a lack or functional deficiency of blood cells, such as leukemia and aplastic anemia. However, stem cells present in parenchymal organs such as the brain, heart or liver are technically difficult to obtain from living tissues and/or to culture in vitro, and such stem cells also generally have low proliferation potency. Stem cells can also be recovered from tissues from corpses, but the medical use of cells obtained in this manner is associated with ethical problems. Consequently, regenerative treatments for neuropathy, cardiopathy and the like will require the development of techniques for generating desired cell types using cells other than stem cells present in such target tissues.

First, methods of utilizing "pluripotent stem cells" may be mentioned as strategies based on this approach. "Pluripotent stem cells" are defined as cells capable of prolonged or virtually indefinite proliferation in vitro while retaining their undifferentiated state, exhibiting normal karyotype (chromosomes) and having the capacity to differentiate into all cell types of the three germ layers (ectoderm, mesoderm and endoderm) under the appropriate conditions. Currently the most commonly known pluripotent stem cells are embryonic stem cells (ES cells) isolated from the early embryo, and the analogous embryonic germ cells (EG cells) isolated from fetal primordial germ cells, both of which are the subjects of ongoing research.

ES cells can be isolated as an undifferentiated stem cell population by transferring the inner cell mass of a blastocyst-stage embryo to in vitro culture and repeating the process of detaching and passaging the cell mass. The cells have suitable cell density on feeder cells prepared from primary cultured murine embryonic fibroblasts (hereinafter, MEF cells) derived from murine fetal tissue or stromal cells such as STO cells, and repeated passaging with frequent replacement of the culture medium can lead to establishment of a cell line retaining the property of undifferentiated stem cells. Another feature of ES cells is the presence of the enzyme telomerase, which exhibits an activity of maintaining chromosomal telomere length, and this enzyme confers to ES cells the capacity for virtually unlimited cell division in vitro.

ES cell lines produced in this manner are "pluripotent" as they can be repeatedly grown and passaged almost indefinitely while maintaining normal karyotype, and they are capable of differentiating into various different cell types. For example, when ES cells are transplanted into an animal body subcutaneously, intraabdominally or intratesticularly they form tumors called "teratomas", but the tumors comprise a mixture of different cells and tissues including neurons, osteocytes, chondrocytes, intestinal cells, muscle cells and the like. In mice, intrauterine transplantation into a pseudopregnant mouse of an aggregate embryo generated by infusion graft of ES cells into a blastocyst-stage embryo or aggregation with an eight-cell stage embryo, results in generation of a "chimeric mouse", which is an offspring possessing differentiated cells derived from the ES cells throughout the entire body or in parts of its organs and tissues. This technique is often used as a main method for generating "knockout mice" having certain genes which are artificially disrupted or modified.

It is also well known that ES cells are induced to differentiate into diverse types of cells by in vitro culturing as well. While the specific method differs depending on the type of cell, it is common to employ a method of inducing differentiation by forming an "embryoid body" (hereinafter, "EB") which is a cell mass in an embryo-like state produced by aggregating ES cells by suspension culture. Such a method can produce cells having fetal stage endoderm, ectoderm and mesoderm characteristics, as well as differentiated cells such as blood cells, vascular endothelial cells, chondrocytes, skeletal muscle cells, smooth muscle cells, cardiomyocytes, glial cells, neurons, epithelial cells, melanocytes, keratinocytes, adipocytes and the like. Differentiated cells produced by in vitro culturing in this fashion have essentially the same structural and functional features as cells present in organs and tissues, and transplant experiments using experimental animals have demonstrated that ES cell-derived cells anchor to organs and tissues and function normally.

For reviews of ES cell properties and culturing methods, and their in vivo and in vitro differentiating abilities, refer to the following literature: Guide to Techniques in Mouse Development (Wasserman et al., Academic Press, 1993); Embryonic Stem Cell Differentiation in vitro (M. V. Wiles, Meth. Enzymol. 225:900, 1993); Manipulating the Mouse Embryo: A Laboratory Manual (Hogan et al., Cold Spring Harbor Laboratory Press, 1994)(Non-patent document 1); Embryonic Stem Cells (Turksen, ed., Humana Press, 2002) (Non-patent document 2).

EG cells can be produced by stimulating fetal germ cells known as primordial germ cells on feeder cells such as MEF cells or STO cells in the same manner as ES cells, using Leukemia Inhibitory Factor (hereinafter, LIF) and basic Fibroblast Growth Factor (hereinafter, bFGF/FGF-2), or chemical agents such as forskolin (Matsui et al., Cell 70:841, 1992; Koshimizu et al., Development 122:1235, 1996). It has been confirmed that EG cells have properties very similar to ES cells and have pluripotency (Thomson & Odorico, Trends Biotechnol. 18:53, 2000). Throughout the present specification, therefore, the term "ES cells" may include "EG cells".

After Thomson et al. first established ES cells from a primate (rhesus monkey) in 1995, the concept of regenerative medicine using pluripotent stem cells began to approach the realm of possibility (U.S. Pat. No. 5,843,780; Proc. Natl. Acad. Sci. USA 92:7844, 1995). Later, the researchers used similar methods to successfully isolate and establish ES cell lines from human early embryos (Science 282:114, 1998). Research groups in Australia and Singapore later submitted similar reports (Reubinoff et al., Nat. Biotech. 18:399, 2000; International Patent Publication No. WO00/27995), and currently 20 different human ES cell lines have been registered at the U.S. National Institutes of Health (NIH)(http://stemcells.nih.gov/registry/index). Also, Gearhart and their colleagues have succeeded in establishing a human EG cell line from human primordial germ cells (Shamblott et al., Proc. Natl. Acad. Sci. USA 95:13726, 1998; U.S. Pat. No. 6,090,622).

When these pluripotent stem cells are used to produce research materials or regenerative medicine products, it is essential that the passaging methods used maintain the undifferentiated state and high proliferation potency of the cells. MEF cells or similar cells (such as STO cells) are usually used as feeder cells for ES/EG cells to maintain the undifferentiated state and high proliferation potency of the cells. Addition of fetal bovine serum (hereinafter, FBS) to the culture medium is also important, and it is crucial to select an FBS product which is suited for the culturing of the ES/EG cells, usually with the addition of FBS at about 10-20%. Also, LIF has been identified as a factor that maintains the undifferentiated state of ES/EG cells derived from mouse embryo (Smith & Hooper, Dev. Biol. 121:1, 1987; Smith et al., Nature 336:688, 1988; Rathjen et al., Genes Dev. 4:2308, 1990), and addition of LIF to culture can more effectively maintain the undifferentiated state (see the following literature: Manipulating the Mouse Embryo: A Laboratory Manual (Hogan et al., Cold Spring Harbor Laboratory Press, 1994 (Non-patent document 1) and Embryonic Stem Cells (Turksen ed., Humana Press, 2002) (Non-patent document 2)).

However, the culturing methods employed for these classical ES/EG cells are not suitable methods when human ES (or EG) cells are used for regenerative medicine or other practical purposes. One reason for this is that human ES cells are unresponsive to LIF, and lack of feeder cells causes death of the cells or loss of the undifferentiated state and differentiation into different cell types (Thomson et al., Science 282:1145, 1998). The use of feeder cells itself is another problem because as such co-culturing systems increase production cost and are poorly suited for large-scale culturing, while separation and purification of the ES cells from the feeder cells is required when the ES cells are to be actually used. In the future, when human ES cells and other pluripotent stem cells are utilized as cell sources for regenerative medicine, and particularly for cell transplantation therapy, the use of non-human animal cell products such as MEF cells and FBS will not be desirable because of risks including potential infection of the ES cells by heterozoic viruses and contamination with antigenic molecules that may be recognized as heteroantigens (Martin et al., Nature Med. 11:228, 2005).

Consequently, in order to refine ES/EG cell culturing methods and modify them to be suitable for future implementation, active efforts are being made to develop FBS substitutes (International Patent Publication No. WO98/30679) and to utilize human cells as feeders instead of MEF cells (Richards et al., Nature Biotech. 20:933, 2002; Cheng et al., Stem Cells 21:131, 2003; Hovatta et al., Human Reprod. 18:1404, 2003; Amit et al., Biol. Reprod. 68:2150, 2003).

Development of culturing methods using no feeders is another alluring prospect. Carpenter and coworkers have reported that seeding of ES cells in a Matrigel- or Laminin-coated culturing plate and addition of MEF cell conditioned medium to the culture medium allows prolonged culturing of human ES cells which retain their undifferentiated and pluripotency (Xu et al., Nature Biotech. 19:971, 2001 (Non-patent document 3); International Patent Publication No. WO01/51616 (Patent document 1)). The same group also succeeded in constructing a more effective ES cell culturing system by developing a serum-free medium containing added bFGF/FGF-2 or Stem Cell Factor (hereinafter, SCF) (International Patent Publication No. WO03/020920 (Patent document 2)). An ES cell culturing system using the same serum-free medium and requiring no feeder has also been reported by an Israeli research group (Amit et al., Biol. Reprod. 70:837, 2004 (Non-patent document 4)).

Recently, a method of maintaining the undifferentiated state of human ES cells by addition of bFGF/FGF-2 and the bone morphogenetic protein antagonist Noggin has also been reported (Xu et al., Nature Methods 2:185, 2005). Separately, it has been shown that simple addition of Glycogen Synthase Kinase (GSK)-3 inhibitor to culture medium can efficiently maintain the undifferentiated state of murine and human ES cells without addition of growth factors or the like and without using feeder cells (Sato et al., Nature Med. 10:55, 2004 (Non-Patent document 5)).

Thus, while new methods are being proposed for culturing of pluripotent stem cells without the use of feeder cells, actual implementation and industrial use of such cells will require even greater convenience of pluripotent stem cell growth effects and culturing methods.

One well known factor that maintains the undifferentiated state of murine ES/EG cells and increases their proliferation potency is the LIF mentioned above, and while the LIF-related IL-6 family of molecules falls under this category (Yoshida et al., Mech. Dev. 45:163, 1994; Koshimizu et al., Development 122:1235, 1996), very few other examples have been reported. Recently, serum-free medium containing added bFGF/FGF-2 or SCF has been reported to notably promote the proliferation potency of human ES cells (International Patent Publication No. WO03/020920 (Patent document 2)).

Given the active, i.e., proliferating, nature of ES cells in comparison to other cell types, few attempts have been made to actually investigate their proliferation potency; however, the needs of regenerative medicine will require increased proliferation of such cells.

One of the problems currently encountered in culturing pluripotent stem cells is that the cells generally form tight colonies and are therefore difficult to handle for passaging and the like. Undifferentiated ES/EG cells are usually found in a condition with the cells firmly adhering to each other, forming colonies, i.e. cell masses with indistinct boundaries between cells. For provision of ES/EG cells for passaging or differentiation-inducing experiments, it is therefore necessary to disperse the colonies in as short a period as possible by treatment with protease solutions of trypsin or the like. When this is done, however, dispersion of the ES/EG cell colonies into individual cells requires relatively high-concentration protease treatment and/or vigorous mechanical stirring, and such procedures significantly reduce the viability and adhesion ability of the ES/EG cells.

Moreover, since ES/EG cells undergo spontaneous differentiation during continuous culturing in a clustered condition, they must be dispersed to single cells during passaging and the passaging must be carried out before colonies grow to an excessive size. Murine ES cells, for example, generally require each passaging to be conducted for 2-3 days, and if the passaging is not conducted by a suitable method, cells that have deviated from their undifferentiated state may appear in the cluster, rendering the cells unsuitable for use. This cannot be overcome simply by adding a sufficient amount of a factor that maintains the undifferentiated state of ES/EG cells, such as the LIF mentioned above or GSK-3 inhibitors, and excessive colony growth and cells with a differentiated phenotype are induced. Therefore, a method of growing ES/EG cells without formation of colonies, i.e., with the cells individually dispersed, is expected to be highly useful for providing ES/EG cells for industrial use. However, no such attempts or successes can be found to date.

In recent years, totipotent cells that can be produced from skin or organ cells without destroying embryos, i.e., induced pluripotent stem cells (iPS cells), have been produced (Patent Document 3, Patent Document 4 and Patent Document 5).

iPS cells have been established in mice and human. Since iPS cells can be obtained without an ethical problem of embryo destruction, and human iPS cells that have been produced using cells from a patient to be treated can be used for differentiation into his/her tissue cells, iPS cells are, especially in the field of regenerative medicine, expected to be a graft material with no rejection. The properties of iPS cells are similar to those of ES cells, and there are problems similar to those of ES cells as described above.

The present inventors have previously seeded F9 cells, an embryonal carcinoma cell line known to normally proliferate by colony formation, on a culture plate coated with E-cadherin (Nagaoka et al., Biotechnol. Lett. 24:1857, 2002 (Non-patent document 6)) and have found that this prevents formation of cell colonies (International Symposium on Biomaterials and Drug Delivery Systems, 2002 Apr. 14-16, Taipei, Taiwan; 1st Meeting of the Japanese Society for Regenerative Medicine, 2002 Apr. 18-19, Kyoto, Japan). Specifically, F9 cells exhibited a dispersed cell morphology on a culturing plate having E-cadherin, which is a known cell adhesion molecule for F9 cells, immobilized on an untreated polystyrene culturing plate (hereinafter, "E-cad plate").

F9 cells exhibit a phenotype somewhat similar to ES cells, expressing alkaline phosphatase (hereinafter, ALP) or SSEA-1 and Oct-3/4, which are known as specific ES/EG cell markers (Lehtonen et al., Int. J. Dev. Biol. 33:105, 1989, Alonso et al., Int. J. Dev. Biol. 35:389, 1991). However, F9 cells do not require feeder cells or LIF for maintenance of the undifferentiated state of the cells, and therefore are different in their mechanism of maintaining undifferentiation. Moreover, whereas ES cells have triploblast differentiating potential to all three germ layers, the differentiation of F9 cells is limited to endodermal cells, and they are unable to form chimeras. In other words, although F9 cells are used as an ES/EG cell model system in some experiments, they differ from ES/EG cells in many aspects involving the culturing method and culturing conditions.

Thus, it was not possible to predict, based on the scientific evidence, whether an E-cad plate can be used in ES cell culturing methods that require no feeder cells, whether ES cells cultured by such methods can be passaged while maintaining their undifferentiated state and pluripotency, and whether the proliferation potency of the ES cells can be increased. In fact, the proliferation potency of F9 cells cultured on an E-cad plate is roughly equivalent to that of F9 cells cultured on a conventional cell culturing plate, and no data had been obtained to suggest that the proliferation potency of ES cells could thereby be increased.

E-cadherin is known to be expressed by undifferentiated murine ES cells, and it is also known that intercellular adhesion is notably inhibited with ES cells that lack E-cadherin gene expression due to gene modification (Larue et al., Development 122:3185, 1996). However, it has not yet been attempted to use E-cadherin as an adhesion substrate in an ES/EG cell culturing method.

In addition to the efficient culturing methods described above, when pluripotent stem cells such as ES cells are to be used as a laboratory material or for production of regenerative medicine products, it is also necessary to design methods for efficiently introducing selected exogenous genes into the cells and expressing them. In particular, one strategy for applying ES cells in regenerative medicine for treatment of various diseases is to modify the cell properties, such as proliferation and differentiation potency or the drug sensitivity, and this can be satisfactorily realized by introducing and expressing appropriate exogenous genes in the cells. In the case of murine ES cells, it is widely known that genes can be artificially modified to produce transgenic mice or knockout mice, for which efficient gene transfer methods are especially useful.

Ordinary transfer of exogenous genes into cells is frequently accomplished using agents such as calcium phosphate, DEAE-dextran and cationic lipid preparations. However, application of such methods to ES cells is known to result in lower efficiency than for other cell types (Lakshmipathy et al., Stem Cells 22:531, 2004 (Non-patent document 8)). Methods using various viral vectors for transfer of exogenous genes have also been reported. For example, retroviral vectors (Chemy et al., Mol. Cell. Biol., 20:7419, 2000), adenovirus vectors (Smith-Arica et al., Cloning Stem Cells 5:51, 2003), lentivirus vectors (Amaguchi et al. J. Virol. 74:10778, 2000; Asano et al., Mol. Ther. 6:162, 2002; International Patent Publication No. WO02/101057), and Sendai virus vectors (Sasaki et al., Gene Ther. 12:203, 2005; Japanese Unexamined Patent Publication No. 2004-344001) are publicly known. Nevertheless, the construction and preparation of viral vectors require relatively complex and time consuming, while biological safety is also an issue, depending on the virus, and therefore such methods are neither convenient nor universally employed.

Consequently, exogenous gene transfer into ES cells is most commonly carried out by a method known as electroporation. This technique involves application of an electrical pulse to cells to transiently open pores in the cell membranes for introduction of an exogenous gene into the cells, and it is a highly flexible method. Recently, an improved technique called nucleofection has been established, whereby an exogenous gene is transferred directly into cell nuclei to achieve significantly higher expression efficiency (Lorenz et al., Biotech. Lett. 26:1589, 2004; Lakshmipathy et al., Stem Cells 22:531, 2004 (Non-patent document 8)). However, this method requires a special electrical pulse-generating device, and it is not easy to prepare the optimal conditions. Furthermore, it is necessary to first treat the cells with a protease such as trypsin to disperse the individual cells, and therefore the cell toxicity is relatively high. Thus, the most useful gene transfer methods for pluripotent stem cells such as ES cells would be methods using gene transfer agents that are inexpensive and convenient to prepare, and would allow efficient transfer of exogenous genes into cells being cultured in an incubator.

Embryonic stem cells (ES cells) and induced pluripotent stem cells (iPS cells) can become unlimited sources for differentiated cells including cells having a neural function, and are representative means promising for overcoming many human diseases. In embryonic development, neurons are generated from neuroectoderm progenitors. Efficient production of these ectodermal progenitor cells can allow on-demand production of various subtypes of neurons.

Many studies have been made in order to produce a specified lineage of neural cells from ES cells or iPS cells. Most of protocols for neural differentiation of ES cells are dependent on formation of so-called embryoid bodies (EBs) or cell clusters such as a spherical neural stem cell mass, at the beginning of differentiation. The studies on induction into a specified lineage of neural cells look promising at first, but subsequent studies proved that the neural cell populations obtained from ES cells or iPS cells contain not only various subtypes of neural cells but also non-neural cells including undifferentiated cells.

RELATED ART DOCUMENTS

Patent Documents

Patent Document 1: International Patent Publication No. WO2001/051616
Patent Document 2: International Patent Publication No. WO2003/020920
Patent Document 3: International Patent Publication No. WO2007/069666
Patent Document 4: International Patent Publication No. WO2009/057831
Patent Document 5: International Patent Publication No. WO2009/075119

Non-Patent Documents

Non-patent Document 1: Manipulating the Mouse Embryo: A laboratory manual (Hogan et al., Cold Spring Harbor Laboratory Press, 1994
Non-patent Document 2: Embryonic Stem Cells (Turksen ed., Humana Press, 2002)
Non-patent Document 3: Xu et al., Nature Biotech., 19:971, 2001
Non-patent Document 4: Amit et al., Biol. Reprod., 70:837, 2004
Non-patent Document 5: Sato et al., Nature Med., 10:55, 2004
Non-patent Document 6: Nagaoka et al., Biotechnol. Lett., 24:1857, 2002
Non-patent Document 7: Nagaoka et al., Protein Eng., 16:243, 2003
Non-patent Document 8: Lakshmipathy et al., Stem Cells, 22:531, 2004

SUMMARY OF THE INVENTION

Problems to be Solved by the Invention

In order to use, as graft materials with no rejection, the totipotent cells described above such as ES cells or iPS cells, it is necessary to differentiate the cells into a specified cell species. In differentiating such totipotent cells into an arbitrary cell species, the homogeneity of the cells after differentiation induction as well as the differentiation-inducing efficiency will be required. In other words, contamination of cells other than cells of interest after differentiation induction such as differentiated cells of no interest or undifferentiated cells is undesirable from the viewpoint of avoiding the risk of malignant transformation after transplantation.

For example, in cases of conventional differentiation induction methods comprising formation of an embryoid body and/or use of feeder cells, there are problems that cells of interest cannot be obtained alone at a high purity, since a cell mass (cell colony) will be formed and cells of all three germ layers are induced inside the mass.

Therefore, an object of the present invention is to provide a cell culture substrate, and a cell culturing method using the substrate and a method for inducing differentiation of pluripotent stem cells using the substrate, which allow culturing of pluripotent stem cells and allow differentiation of pluripotent stem cells into a specified cell species, particularly neural and neural progenitor cells, at a high purity.

Means for Solving the Problems

The present inventors intensively studied in view of the above to discover that the above-described problems can be solved by using a cell culture substrate whose surface is immobilized or coated with a certain protein(s), thereby completing the present invention.

Regulation of stem cell behavior and formation of appropriate neural circuits are dependent on the complex interaction between an extracellular inducing factor(s) and the intracellular signaling. E-cadherin and N-cadherin belonging to cadherin superfamily are extracellular adhesion molecules respectively involved in the pluripotency and neurogenesis of ES cells, and have been the most studied among those. Recently, it has been proved that E-cadherin plays important roles in maintaining pluripotency, suppressing heterogeneity of cells, and generating iPS cells. Moreover, N-cadherin functions as an important regulator of nervous system development by providing important molecular signals in many developmental processes such as retinal development, somite formation and neurite outgrowth. These cadherins are expressed in various modes according to development stages and/or cell types. Murine (m) ES cells and iPS cells express E-cadherin at high levels, which can be a marker of their pluripotency. On the other hand, neural differentiation of mES cells is associated with the switching from E-cadherin to N-cadherin, up-regulation of E-cadherin repressor molecules, and increased cell motility.

The present inventors have obtained neural cell populations of high purity by using an N-cadherin fusion protein as an extracellular matrix and by direct differentiation from P19 embryonal carcinoma cells or neural stem cells. In order to avoid the use of carcinoma cells and increase the differentiation rate, the present inventors induced feeder-dependent mES cells and miPS cells into neuroectoderm progenitors. The mES and iPS cells on cadherin-based artificial extracellular matrices exhibited a more excellent totipotency compared to that of the cells on natural substrata. The homogeneous populations of the undifferentiated mES or iPS cells were ideal for generating neural progenitors under completely-controlled culturing conditions. In addition, the present inventors have discovered that efficient monolayer differentiation can be induced by using as an artificial extracellular matrix two fusion proteins of cadherin family proteins, most preferably two fusion proteins of E-cadherin-Fc and N-cadherin-Fc, in combination.

That is, the present invention is the following [1] to [14], which relate to a cell culture substrate, and a cell culturing method using the substrate and a method for inducing differentiation of pluripotent stem cells using the substrate.

[1] A cell culture substrate, characterized in that, onto the surface, one or more selected from the group consisting of N-cadherin, a fusion protein comprising an entire or partial region of N-cadherin, and a fusion protein comprising an entire or partial region of a protein homologous to N-cadherin are immobilized or coated.

[2] The cell culture substrate of [1], wherein one or more selected from the group consisting of a protein belonging to cadherin family, a fusion protein comprising an entire or partial region of a protein belonging to cadherin family, and a fusion protein comprising an entire or partial region of a protein homologous to a protein belonging to cadherin family are further immobilized or coated onto the surface.

[3] The cell culture substrate of [2], wherein said protein belonging to cadherin family is E-cadherin.

[4] The cell culture substrate of [2] or [3], wherein a fusion protein comprising an entire or partial region of E-cadherin or a protein homologous to E-cadherin, and a fusion protein comprising an entire or partial region of N-cadherin or a protein homologous to N-cadherin are immobilized or coated onto the surface.

[5] The cell culture substrate of any one of [1] to [4], wherein said protein homologous to N-cadherin is a protein which comprises one or more of the EC1 domain, EC2 domain, EC3 domain, EC4 domain and EC5 domain, and which has homophilic binding ability with N-cadherin.

[6] The cell culture substrate of any one of [3] to [5], wherein said protein homologous to E-cadherin is a protein which comprises one or more of the EC1 domain, EC2 domain, EC3 domain, EC4 domain and EC5 domain, and which has homophilic binding ability with E-cadherin.

[7] The cell culture substrate of any one of [1] to [6], wherein the fusion protein comprising an entire or partial region of N-cadherin or a protein homologous to N-cadherin is a fusion protein of an entire or partial region of N-cadherin or a protein homologous to N-cadherin and an immunoglobulin Fc region.

[8] The cell culture substrate of any one of [3] to [7], wherein the fusion protein comprising an entire or partial region of E-cadherin or a protein homologous to E-cadherin is a fusion protein of an entire or partial region of E-cadherin or a protein homologous to E-cadherin and an immunoglobulin Fc region.

[9] A cell culture substrate, characterized in that, onto the surface, two or more selected from the group consisting of a protein belonging to cadherin family and a fusion protein comprising an entire or partial region of a protein belonging to cadherin family are immobilized or coated.

[10] The cell culture substrate of any one of [1] to [9], which is used for culturing for induction into neural progenitor cells or neural cells.

[11] A cell culturing method, characterized by growing pluripotent stem cells using the cell culture substrate of any one of [1] to [9] and a liquid medium while maintaining their undifferentiated state and pluripotency.

[12] A method for inducing differentiation of pluripotent stem cells, characterized by differentiating pluripotent stem cells using the cell culture substrate of any one of [1] to [9] and a liquid medium containing a differentiation-inducing factor(s).

[13] The method for inducing differentiation of pluripotent stem cells of [12], by which pluripotent stem cells are differentiated into neural progenitor cells or neural cells.

[14] A method of producing neural progenitor cells or neural cells, characterized by culturing ES cells or iPS cells on the cell culture substrate of any one of [1] to [9] using a liquid medium containing a differentiation-inducing factor(s).

Effects of the Invention

By the present invention, it is possible to provide a cell culture substrate, and a cell culturing method using the substrate and a method for inducing differentiation of pluripotent stem cells using the substrate, which allow culturing of pluripotent stem cells without using feeder cells, allow differentiation of pluripotent stem cells into a specified cell species, particularly neural and neural progenitor cells, at a high purity, and can also be used for selection of cells after the differentiation.

In addition, in cases where pluripotent stem cells are cultured on the cell culture substrate of the present invention, generation of cell aggregates are suppressed and the cells can be cultured while maintaining the single-cell-dispersing morphology. This facilitates grasp of the differentiation stages by morphological observation. The present invention also allows to suppress generation of cells that remain undifferentiated during the differentiation induction and to culture for differentiation induction while maintaining the homogeneity of cell populations, and therefore provision of desired cells at a high purity can be expected.

(B) The adhesion of the ES cells on E-cad-Fc substrata was integrin-independent. The cells seeded onto gelatin substrata or E-cad-Fc substrata were cultured in the presence of 15% KSR or 15% FBS for 16 hours. Total FAK (tFAK) and phosphorylated FAK (pFAK) of the mES cells were confirmed by Western blotting using monoclonal anti-FAK antibody and monoclonal anti-pFAK antibody, respectively.

(C) Adhesion of the miPS cells in the absence of FBS. The iPS cells cultured on E-cad-Fc substratum for 6 hours by using an undifferentiating medium containing 15% KSR had an adhesion ratio higher than that of the iPS cells cultured on type I collagen substratum.

(D) Phase contrast micrographs of the mES cells and the miPS cells cultured in various media for 4 days. The cells were stained in order to examine the alkaline phosphatase activity. The upper 4 micrographs are of the mES cells, and the lower 4 micrographs are of the miPS cells (in these 4 micrographs, upper left: gelatin substrata; lower left: type I collagen substrata; upper right: fibronectin; and lower right: E-cad-Fc substrata).

(E) Flow cytometry profiles of Nanog protein expression in miPS cells cultured for 4 days on 4 different substrata.

(F) Fluorescence micrographs showing the results of immunostaining for SSEA1 protein expression in mES cells (i-iv) and miPS cells (v-viii) cultured for 2 days on gelatin substrata or E-cad-Fc substrata.

(G) Results obtained by examining by RT-PCR the expression of a pluripotency marker (Oct3/4), an ectoderm marker (Sox1), mesendoderm markers (Gsc and Bra), endoderm markers (Foxa2, Sox17 and Gata6) and a mesoderm marker (Gata1) in spontaneously differentiated feeder-independent mES cells (EB3) and feeder-dependent iPS cells.

Figure 2:
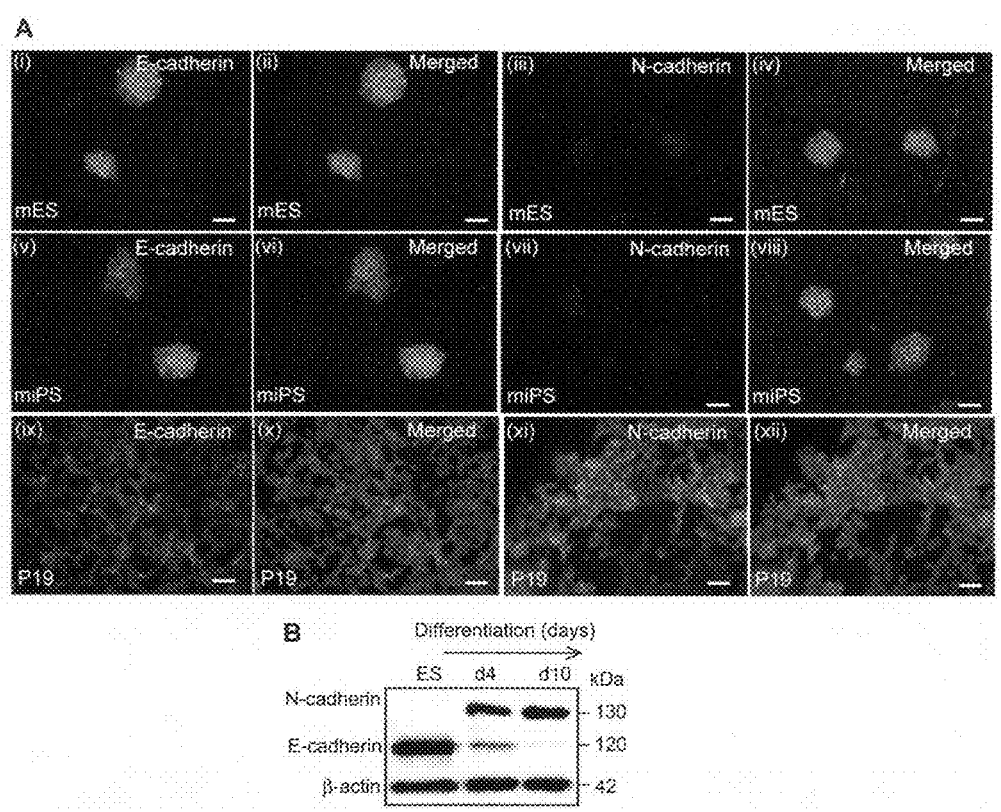

FIG. 2(A) is fluorescence micrographs showing expression patterns of E-cadherin and N-cadherin proteins on the surface of undifferentiated cells. mES cells (i-iv) and miPS cells (v-viii) were cultured for 2 days in the presence of LIF, and the expression of E-cadherin and N-cadherin proteins was examined by immunostaining. P19 cells were used as a control (the lower 4 micrographs). The bars indicate 50 μm.

FIG. 2(B) is a photograph showing the result of Western blotting. Total E-cadherin or N-cadherin expression in the mES cells after inducing the differentiation for 4 or 10 days by a hanging drop method was examined. The left lane was of mES cells used as a control.

Figure 3:
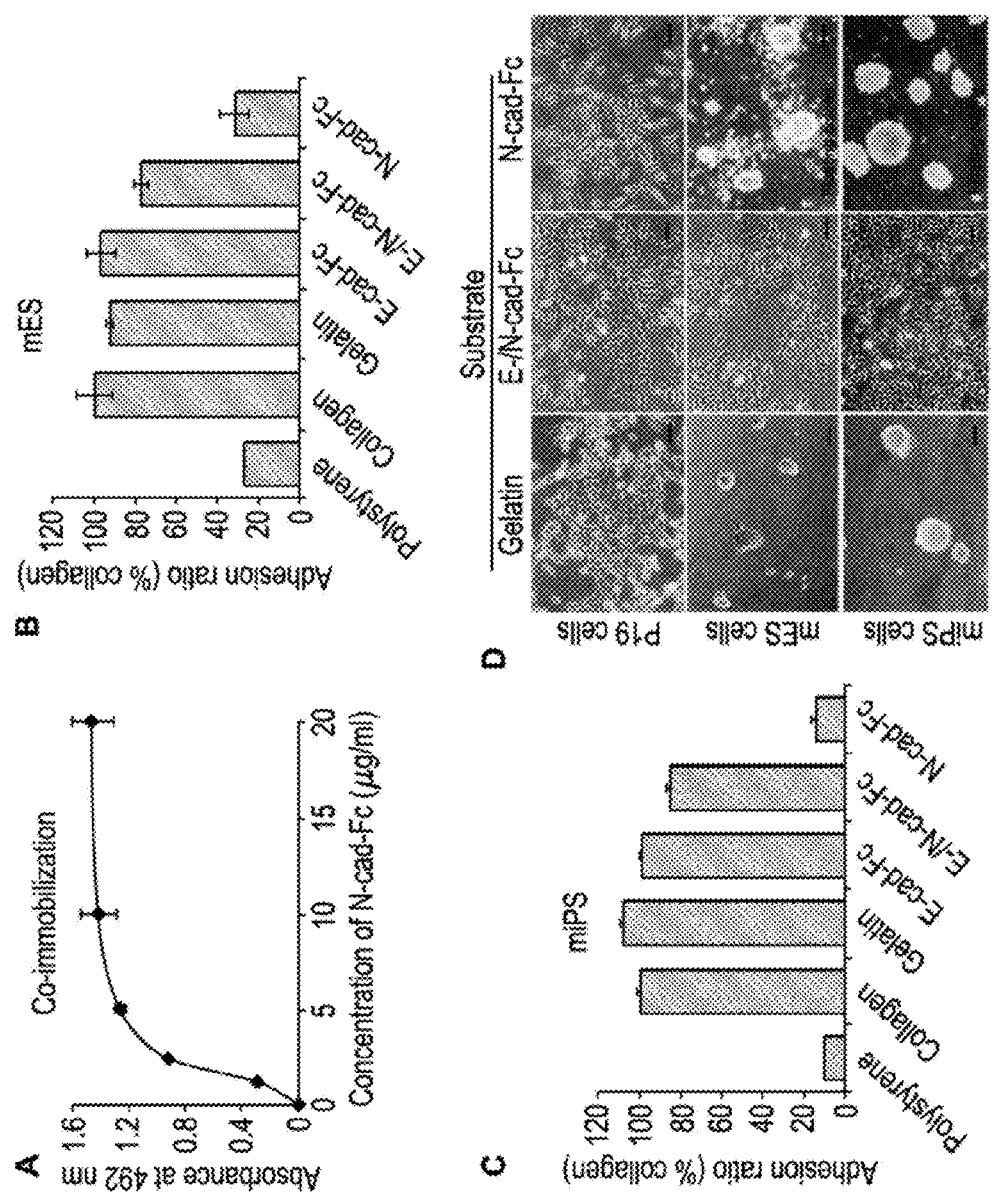

FIG. 3 shows the results obtained by examining adsorption of mES cells and miPS cells onto substrata immobilized with fusion proteins and morphology of these cells thereon.

(A) A graph showing the result obtained by examining by ELISA the co-immobilization of E-cad-Fc and N-cad-Fc onto a polystyrene surface.

(B) A graph showing adsorption of mES cells onto various extracellular matrices. From the left, shown are the results in cases of polystyrene alone, substrata coated with 0.018% type I collagen, substrata coated with 0.1% gelatin, substrata coated with 10 μg/ml E-cad-Fc, substrata coated with 5 μg/ml E-/N-cad-Fc, and substrata coated with 10 μg/ml N-cad-Fc, in the order mentioned.

(C) A graph showing adsorption of miPS cells onto various extracellular matrices. The order of the results shown is the same as in (B). The ES cells and the iPS cells had similar adsorption properties on E-/N-cad-Fc co-immobilized substrata (~85%).

(D) Micrographs showing the results of morphological observation of ES cells and iPS cells cultured on gelatin substrata, E-/N-cad-Fc co-immobilized substrata or N-cad-Fc substrata. P19 cells were used as a control (the upper 3 micrographs). The bars indicate 50 μm.

Figure 4:
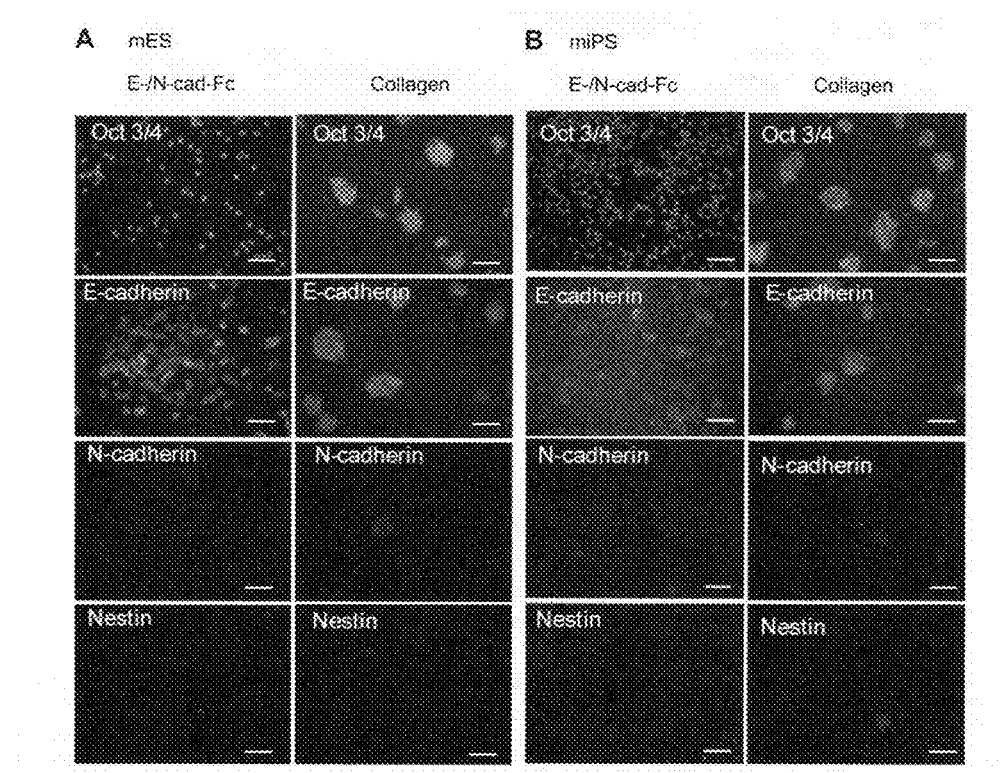

FIG. 4 shows the effect of E-/N-cad-Fc co-immobilized substrata on mES cells and miPS cells in undifferentiated state. Micrographs showing the results of immunostaining. It was shown that the undifferentiated cell markers (Oct3/4 and E-cadherin) exist and the neural progenitor cell markers (N-cadherin and nestin) do not exist in mES cells and miPS cells cultured for 2 days in the presence of LIF on E-/N-cad-Fc co-immobilized substrata.

Figure 5:
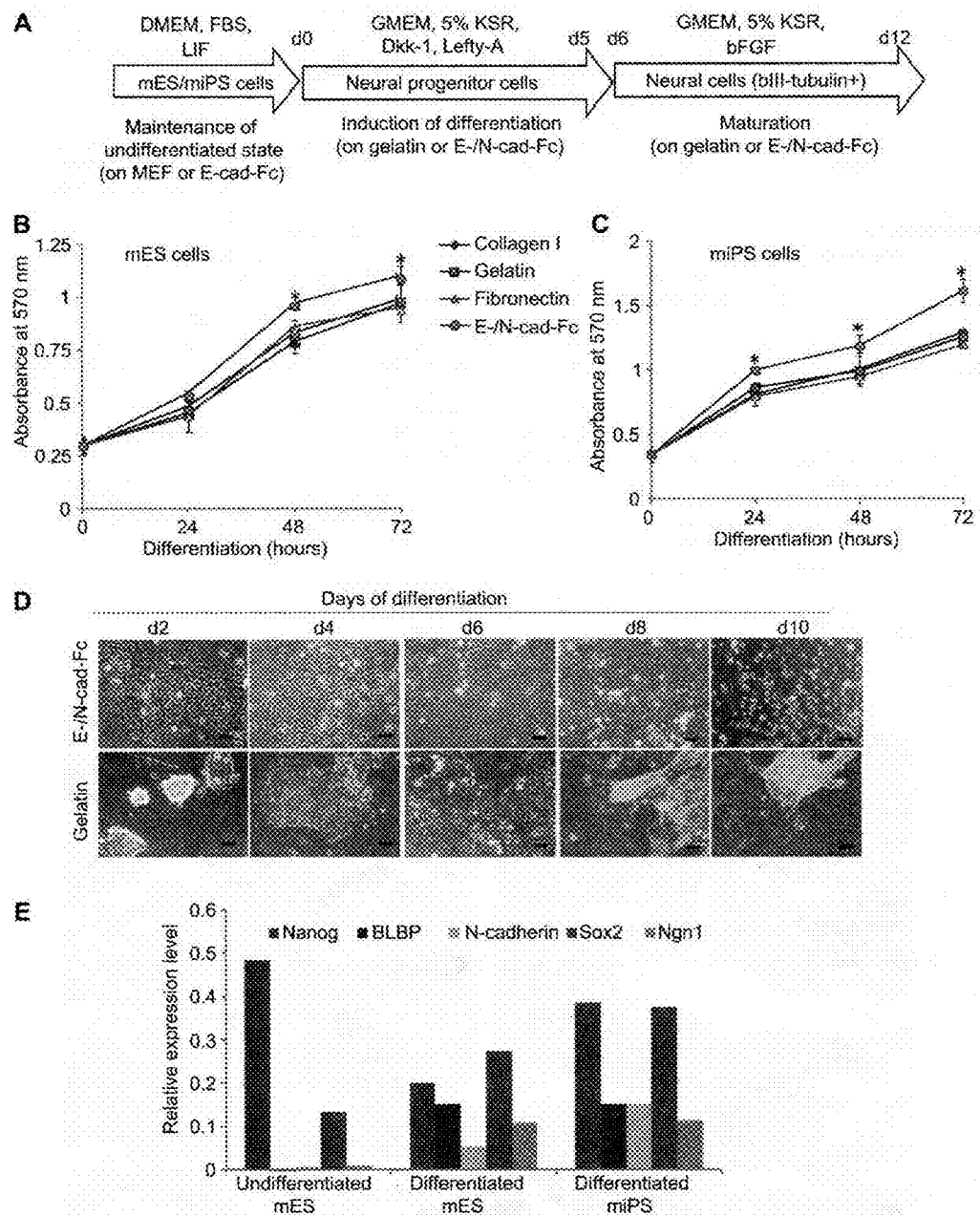

FIG. 5 shows that neural differentiation of mES cells and miPS cells can be induced under homogeneous culturing conditions on E-/N-cad-Fc co-immobilized substrata.

(A) Schematic representation illustrating procedures for differentiation of mES cells and miPS cells into neural cells.

(B) A graph showing proliferation of mES cells cultured on various substrata. The mES cells were seeded at $1 \times 10^4$ cells/well onto a 24-well dish coated with collagen, gelatin, fibronectin or E-/N-cad-Fc. Each well contained neural differentiation medium to which Dkk-1 and Lefty-A were added.

(C) A graph showing proliferation of miPS cells cultured on various substrata. The miPS cells were seeded at $1 \times 10^4$ cells/well onto a 24-well dish coated with collagen, gelatin, fibronectin or E-/N-cad-Fc. Each well contained neural differentiation medium to which Dkk-1 and Lefty-A were added.

(D) Bright field micrographs showing morphological changes of mES cells and miPS cells cultured on 0.1% gelatin substrata or 10 μg/ml E-/N-cad-Fc co-immobilized substrata. In the cells cultured on E-/N-cad-Fc co-immobilized substrata, prominent morphological changes into radial glial cell-like cells were observed within 4 days after the beginning of the differentiation-inducing culturing. Within 10 days after the beginning of the differentiation-inducing culturing, neurite outgrowth was observed. In the cells cultured on gelatin substrata, cell clusters were formed and heterogeneous populations containing cells with neurite outgrowth were observed. The bars indicate 50 μm.

(E) A graph showing the results of semi-quantitative RT-PCR, using Nanog, BLBP, N-cad, Sox2 and Ngn1 markers, and cells on day 2 of the differentiation-inducing culturing. mRNAs obtained from undifferentiated mES cells were used as a control. The expression levels were normalized using that of β-actin, a house-keeping gene. In this graph, from the left for each cell species, shown are the results in cases of Nanog, BLBP, N-cadherin, Sox2 and Ngn1, in the order mentioned.

Figure 6:
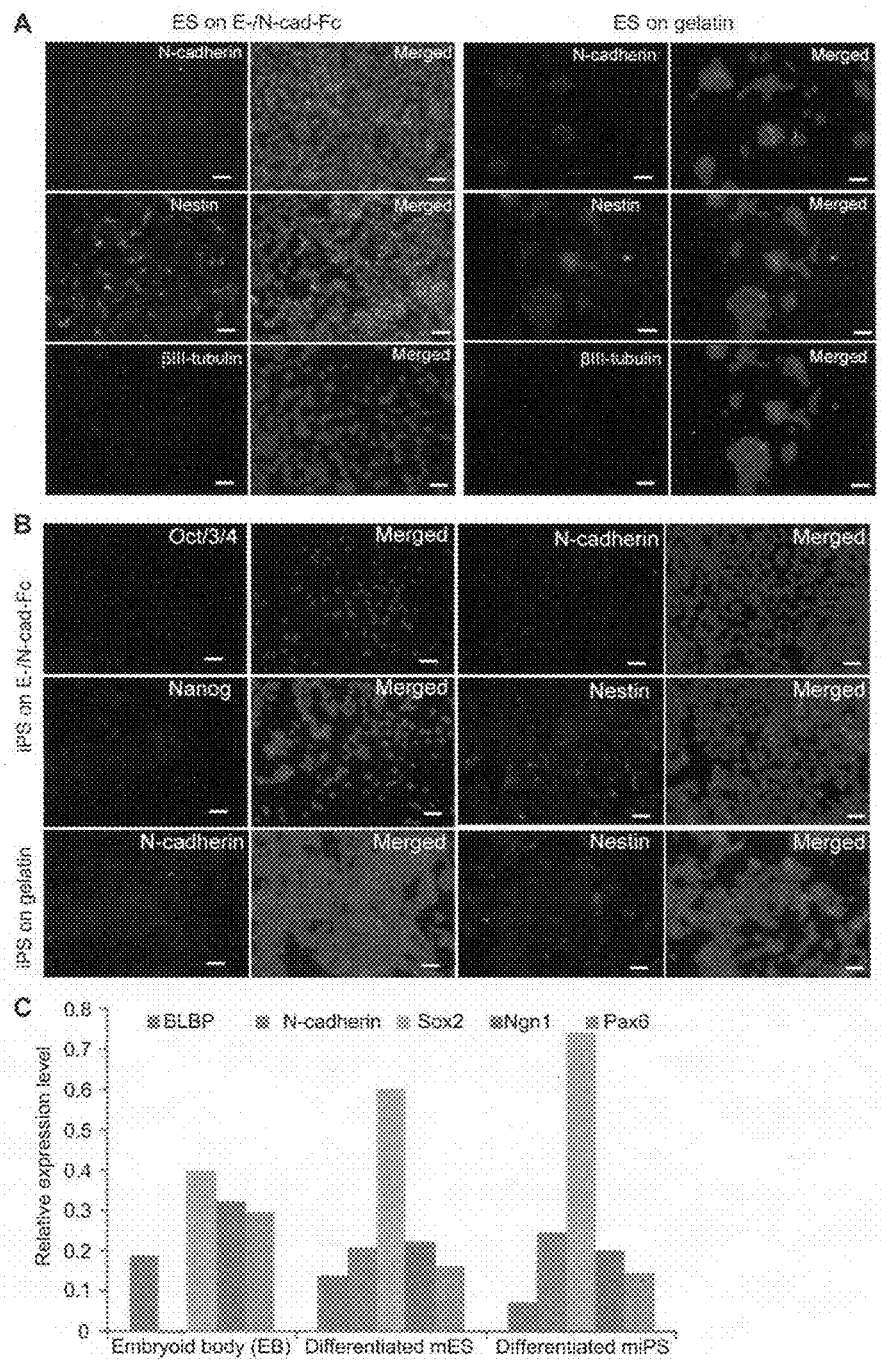

FIG. 6 shows the confirmation results of differentiation into primitive neural stem cells by immunocytochemical analysis and transcription factor gene expression analysis.

(A) Fluorescence micrographs showing the results of immunofluorescent staining of mES cells cultured on an E-/N-cad-Fc co-immobilized substratum or a gelatin substratum. In the mES cells on 4 days after the beginning of the differentiation induction, the expression amount of N-cadherin was low, and nestin was slightly expressed. No expression of βIII-tubulin was observed.

(B) Fluorescence micrographs showing the results of immunofluorescent staining of miPS cells cultured on an E-/N-cad-Fc co-immobilized substratum or a gelatin substratum. In the miPS cells on 4 days after the beginning of the differentiation induction, the expression amounts of the pluripotency markers (Oct3/4, Nanog) were decreased, and the expression amount of N-cadherin was low. Nestin was slightly expressed.

(C) A graph showing the results of semi-quantitative RT-PCR, using BLBP, N-cad, Sox2, Ngn1 and Pax6 markers, and cells on 4 days after the beginning of the differentiation induction. Spontaneously differentiated ES cells were used as a control (EB). The expression levels were normalized using that of β-actin, a house-keeping gene. In this graph, from the left for each cell species, shown are the results in cases of BLBP, N-cad, Sox2, Ngn1 and Pax6, in the order mentioned.

Figure 7:
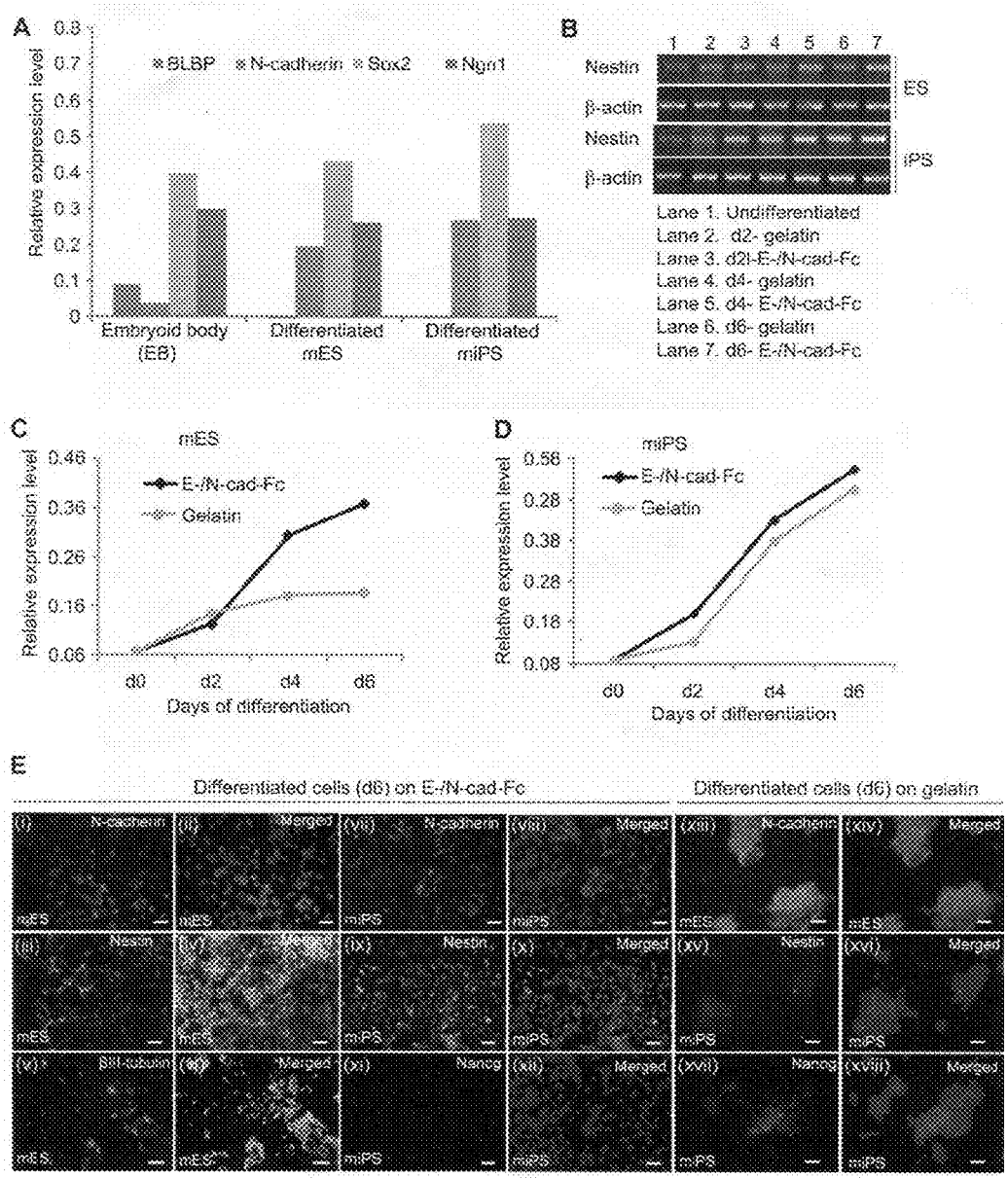

FIG. 7 shows the results obtained by examining differentiation of mES cells and miPS cells into neural progenitor cells.

(A) A graph showing the results of RT-PCR in order to examine the expression amounts of BLBP, N-cad, Sox2 and Ngn1 in mES cells and miPS cells on 6 days after the beginning of the differentiation induction. The fluorescence intensities were quantified using ImgaeQuant software. Spontaneously differentiated ES cells were used as a control (EB).

(B) A photograph showing the RT-PCR results in order to examine the expression amounts of nestin (a neural progenitor cell marker) in mES cells and miPS cells cultured on gelatin substrata or E-/N-cad-Fc co-immobilized substrata. The "d2", "d4" and "d6" respectively represent day 2, day 4 and day 6 after the beginning of the culturing.

(C) A graph showing the results obtained by quantifying with ImageQuant the fluorescence intensities of each band in the results of mES cells in above (B). The expression levels were normalized using that of β-actin, a house-keeping gene.

(D) A graph showing the results obtained by quantifying with ImageQuant the fluorescence intensities of each band in the results of miPS cells in above (B). The expression levels were normalized using that of β-actin, a house-keeping gene.

(E) Fluorescence micrographs showing the results of immunofluorescent staining of mES cells and miPS cells cultured for 6 days on gelatin substratum substrata or E-/N-cad-Fc co-immobilized substrata for the differentiation induction. In the mES cells (i-vi) and the miPS cells (vii-xii) cultured for 6 days on E-/N-cad-Fc co-immobilized substrata for the differentiation induction, the expression amounts of N-cadherin and nestin were higher than those of the cells cultured on gelatin substrata. The expression amount of βIII-tubulin was high in the mES cells cultured on E-/N-cad-Fc co-immobilized substrata (v, vi). No expression of Nanog was observed in the miPS cells cultured on E-/N-cad-Fc co-immobilized substrata (xi, xii). On the other hand, in the miPS cells cultured on gelatin substrata (xvii, xviii), a part of the cells in the colonies did not differentiate, and expressed Nanog, a pluripotency marker. The bars indicate 50 μm.

Figure 8:
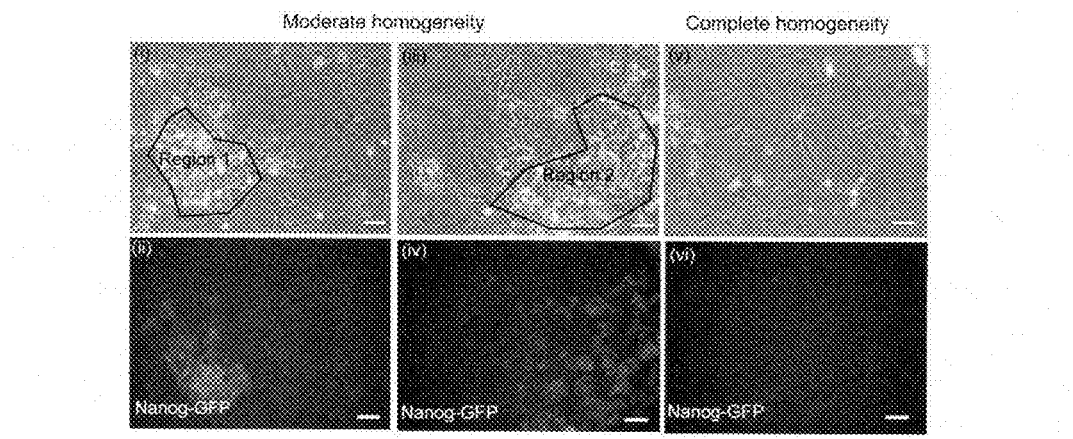

FIG. 8 shows that the loss of Nanog expression was asynchronous within heterogeneous cell populations wherein cells were aggregating. Two different culturing conditions (low cell density and high cell density) were applied to the culturing using E-/N-cad-Fc substrata. miPS cells under the high density conditions (in which $2\times10^4$ cells were seeded on a 35 mm culture dish) formed aggregates, and some of the aggregated cells (Region 1 and Region 2 in this figure) did not differentiate and retained Nanog expression even on 6 days after the beginning of differentiation induction (i-iv). Under the low density conditions (in which $5\times10^3$ cells were seeded on a 60 mm culture dish), homogeneous cell populations were constituted, and Nanog expression was disappeared on 6 days after the beginning of differentiation induction (v, vi). The bars indicate 50 μm.

Figure 9:
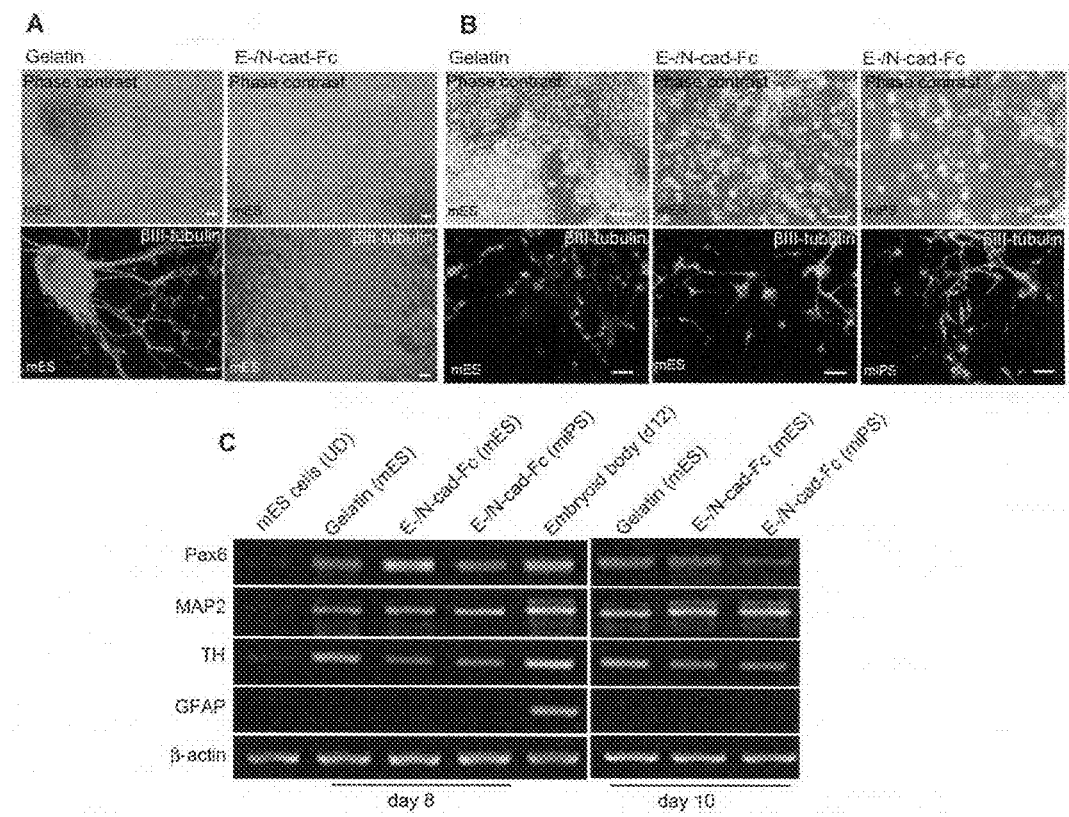

FIG. 9 shows differentiation of neural progenitor cells into βIII-tubulin-expressing neural cells. On 12 days after the beginning of differentiation induction, βIII-tubulin staining of mES cell-derived neural cells and miPS cell-derived neural cells was carried out. Two different culturing conditions (low density and high density) were employed.

(A) mES cells on an E-/N-cad-Fc co-immobilized substratum under the high density conditions (in which $2\times10^4$ cells were seeded on a 35 mm culture dish) exhibited confluent growth and neurite outgrowth covering the entire surface of the substratum. mES cells on a gelatin substratum under the high density conditions (in which $2\times10^4$ cells were seeded on a 35 mm culture dish) formed neurites elongated from cell aggregates. The bars indicate 200 μm.

(B) mES cells and miPS cells cultured on gelatin substrata or E-/N-cad-Fc co-immobilized substrata under the low density conditions (in which $5\times10^3$ cells were seeded on a 60 mm culture dish) expressed βIII-tubulin.

(C) A photograph showing the results obtained by examining the expression of Pax2, MAP2, TH and GFAP by RT-PCR. RT-PCR was carried out using mES cells cultured on gelatin substrata, mES cells cultured on E-/N-cad-Fc co-immobilized substrata, and miPS cells cultured on E-/N-cad-Fc co-immobilized substrata on 8 days (day 8) and 10 days (day 10) after the beginning of the differentiation induction. As controls, undifferentiated mES cells (UD) and spontaneously differentiated ES cells (Embryoid body d12) were used.

MODE FOR CARRYING OUT THE INVENTION

Definitions

The term "pluripotent stem cells" as used throughout the present specification refers to cells capable of prolonged or virtually indefinite proliferation in vitro while retaining their undifferentiated state, exhibiting normal karyotype (chromosomes) and having the capacity to differentiate into all three germ layers (ectoderm, mesoderm and endoderm) under the appropriate conditions. The term "pluripotent stem cells" includes, but is not limited to, ES cells isolated from early embryo, iPS cells and their analogous EG cells isolated from fetal-stage primordial germ cells. Throughout the present specification, "ES cells" will be used to include "EG cells".

The term "undifferentiated state" as used throughout the present specification means the nature of pluripotent stem cells exhibiting a state of undifferentiation that can be confirmed based on one or more undifferentiated ES cell markers such as ALP activity or Oct-3/4 gene (product) expression, or based on expression of various antigenic molecules. The state of undifferentiation of pluripotent stem cells means that the pluripotent stem cells are capable of prolonged or virtually indefinite proliferation and exhibit normal karyotype (chromosomes), while having the capacity to differentiate into all three germ layers under the appropriate conditions.

The term "pluripotency" as used throughout the present specification refers to the ability to differentiate into a variety of cell types. The differentiated cells are not particularly restricted as long as they are of a cell type in which differentiation can generally be induced from pluripotent stem cells. Specifically, there may be mentioned ectodermal cells or ectoderm-derived cells, mesodermal cells or mesoderm-derived cells, endodermal cells or endoderm-derived cells, and the like.

The term "liquid medium" as used throughout the present specification includes any liquid medium that can be used for conventional methods of passaging pluripotent stem cells.

As culture substrates for the present invention, there may be used any ones that are conventionally used for cell culturing, such as a dish (culture dish), a 96-well or 48-well microplate, a plate or a flask. These culture substrates may be made of inorganic materials such as glass, or of organic materials such as polystyrene or polypropylene, but they are preferably sterilizable materials with high heat resistance and moisture resistance.

The method applied for immobilizing or coating the protein belonging to cadherin family, such as N-cadherin or E-cadherin, onto the solid phase surface of the culture substrate may be a physical method such as adsorption or a chemical method such as covalent bonding, but an adsorption method is preferred for ease of operation. The adsorption can be achieved by contacting the substrate surface and a solution containing the protein belonging to cadherin family for a prescribed period of time, preferably for from a few hours to a full day/night period, more preferably for 1 hour to 12 hours. Also, an artificial antigenic molecule may be added to or fused with the adhering molecule beforehand in order to utilize binding of specific antibodies for the antigenic molecule. In this case, the specific antibodies must be immobilized or coated on the solid phase surface of the culture substrate beforehand by a physical method such as adsorption or a chemical method such as covalent bonding. The solid phase surface of the culture substrate onto which the protein is immobilized or coated may be also referred to as a substratum, matrix or extracellular matrix (ECM).

The culture substrate prepared in this manner can be used directly for ordinary culturing of the pluripotent stem cells. That is, an appropriate number of pluripotent stem cells may be suspended in a commonly employed liquid medium or cell culture medium, and the mixture seeded or added onto the culture substrate. Subsequent liquid medium replacement and passaging may also be carried out in the same manner as in conventional methods.

The term "homophilic binding" as used throughout the present specification refers to cell-cell or cell-substrate binding via adhesion molecules that involves binding or association between the same type of adhesion molecule.

The term "feeder cells" as used throughout the present specification refers to separate cells, also known as support cells, that are cultured beforehand and perform the role of supplying nutrients and growth factors which are missing in the medium used for culturing cells which would be unable to survive and grow on their own. "Feeder cells" include, but are not limited to, MEF cells and stromal cells such as STO cells.

The term "dispersed state" as used throughout the present specification refers to a state of growing cells adhered to a culture substrate surface, wherein no distinct colonies are formed and the individual cells are either not in contact with other cells or if partially in contact, have a very small area of contact.

The term "gene" as used throughout the present specification means genetic material, and refers to nucleic acid including transcription units. A gene may be of RNA or DNA, and may be a naturally occurring or artificially designed sequence. Also, the gene need not code for a protein necessarily, and for example, it may code for functional RNA such as a ribozyme or siRNA (short/small interfering RNA).

Other advantages and features of the invention in addition to the effect described above will be explained in the detailed description of the preferred embodiments provided hereunder.

[Cell Culture Substrate]

The cell culture substrate of the present invention is characterized in that, onto the surface, one or more selected from the group consisting of N-cadherin, a fusion protein comprising an entire or partial region of N-cadherin, and a fusion protein comprising an entire or partial region of a protein homologous to N-cadherin are immobilized or coated.

Further, the cell culture substrate of the present invention is preferably one wherein one or more selected from the group consisting of a protein belonging to cadherin family, a fusion protein comprising an entire or partial region of a protein belonging to cadherin family, and a fusion protein comprising an entire or partial region of a protein homologous to a protein belonging to cadherin family, other than N-cadherin mentioned above, are further immobilized or coated onto the surface.

The protein belonging to cadherin family other than N-cadherin mentioned above is preferably E-cadherin.

Cadherins are adhesion molecules involved in $Ca^{2+}$-dependent intercellular adhesion and binding known as adhesive binding or adherens junction binding, and, as examples thereof, the three types, E (epithelial)-cadherin, N (neural)-cadherin and P (placental)-cadherin are known. These cadherin molecules are membrane-bound glycoproteins composed of 700-750 amino acid residues, and the extracellular region comprises five repeating structures, known as extracellular cadherin (EC) domains, consisting of about 110 amino acid residues. For example, the domains of human E-cadherin are EC1, EC2, EC3, EC4 and EC5, respectively corresponding to amino acid residues 157-262, 265-375, 378-486, 487-595 and 596-700. Also, the domains of murine E-cadherin are EC1, EC2, EC3, EC4 and EC5, respectively corresponding to amino acid residues 159-264, 267-377, 380-488, 489-597 and 598-702. These EC domains are homologous among different cadherin molecules, with particularly high homology between the domains situated near the N-terminal (EC1, EC2). Currently, more than 50 cadherin molecules are known to exhibit such similar structure, and these have been grouped together as the cadherin family. Reviews on cadherins may be found in Takeichi, Curr. Opin. Cell Biol., 7:619, 1995; Marrs & Nelson, Int. Rev. Cytol., 165:159, 1996; Yap et al., Annu. Rev. Cell Dev. Biol., 13:119, 1997; Yagi & Takeichi, Genes Dev., 14:1169, 2000; Gumbiner, J. Cell Biol., 148:399, 2000; and elsewhere.

N-cadherin is a ~140 kD protein belonging to calcium-dependent cell adhesion molecules. N-cadherin plays important roles in cell adhesion by interacting with the same cadherin species and associating with the actin cytoskeleton via catenin, and is involved in the development and differentiation stages. N-cadherin is expressed in various tissues including nerves, cardiac muscles, skeletal muscles and vascular endothelium. N-cadherin has reported to function as an important regulator of nervous system development by providing important molecular signals in many developmental processes such as retinal development, somite formation and neurite outgrowth (Miyatani et al., Science, 1989; 245; 631-5, Hansen et al., Cell Mol. Life Sci., 2008:65; 3809-21).

E-cadherin (also, cadherin-1) is widely expressed in epithelial cells such as parenchymal cells of internal organs such as the liver, kidneys and lungs, and in keratinocytes, and it is known to be an important adhesion molecule for intercellular adhesion (see reviews in Mareel et al., Int. J. Dev. Biol. 37:227, 1993; Mays et al., Cold Spring Harb. Symp. Quant. Biol. 60:763, 1995; El-Bahrawy & Pignatelli, Microsc. Res. Tech. 43:224, 1998; Nollet et al., Mol. Cell. Biol. Res. Commun. 2:77, 1999). Also, E-cadherin is abundantly expressed on undifferentiated murine ES cells, and it is known that ES cells lacking E-cadherin expression due to genetic engineering have notably inhibited intercellular adhesion (Larue et al., Development 122:3185, 1996). Moreover, it can be confirmed that E-cadherin genes are also expressed in human ES cell lines, based on data stored at the public gene expression database at the U.S. National Center for Biotechnology Information (NCBI).

The method of producing the protein belonging to cadherin family is not particularly restricted, but preferably involves production, purification and use of a recombinant protein using molecular biological techniques. Other methods with comparable results may be employed, and, for example, a pluripotent stem cell protein belonging to cadherin family may be used after extraction and purification from living tissue or cells, or a peptide thereof may be chemically synthesized for use.

For the proteins belonging to cadherin family, standard protocols have already been established for methods of producing recombinant proteins and obtaining genes coding for the molecules, and reference may be made to the literature cited above, although there is no restriction thereto. Taking E-cadherin as an example, the E-cadherin gene has already been isolated and identified for animals including human, mouse and rat, and the respective nucleotide sequences are accessible from public DNA databases such as NCBI (Accession Nos.: (human) NM_004360; (mouse) NM_009864; (rat) NM_031334). A person skilled in the art can therefore design a primer or probe specific for the E-cadherin gene of interest and use it in ordinary molecular biological techniques to obtain and use cDNA for the E-cadherin gene. Alternatively, cDNA for the E-cadherin gene may be obtained from the RIKEN Gene Bank (Tsukuba, Japan) or the American Type Culture Collection (ATCC), or Invitrogen/ResGen. The gene coding for the protein belonging to cadherin family to be used is preferably derived from the same animal species from which the pluripotent stem cells are derived, and, for example, when the invention is carried out using murine ES cells, it is preferred to use cDNA of murine E-cadherin. However, E-cadherin cDNA derived from different animal species, such as human, monkey, cow, horse, pig, sheep, bird (for example, chicken) or amphibian (for example, *Xenopus laevis*) may be used. Other cadherins, such as N-cadherin (NCBI Accession No.: human NM_001792, mouse NM_M31131, M22556 and the like), may also be used.

An example of a suitable method for producing a recombinant protein of the protein belonging to cadherin family is characterized by transferring a gene coding for the molecule into mammalian cells such as COS cells, 293 cells or CHO cells and expressing it. Preferably, the gene is linked with a nucleic acid sequence allowing transcription and expression of the gene in a wide range of mammalian cells, i.e., a promoter sequence, in a manner so that transcription and expression are under the control of the promoter. The gene to be transcribed and expressed is also preferably linked to a polyA addition signal. As preferred promoters, there may be mentioned promoters from viruses such as SV (Simian Virus) 40 virus, cytomegalovirus (CMV) or Rous sarcoma virus, or β-actin promoter, EF (Elongation Factor) 1α promoter or the like.

The gene used to produce the recombinant protein does not necessarily have to contain the full-length region of the gene coding for the molecule, as it may be a partial gene sequence as long as the protein or peptide molecule encoded by the partial sequence has adhesion activity equivalent to or exceeding that of the original molecule. For example, an E-cadherin suitable for use according to the invention may be a recombinant protein constructed from partial sequences including 690-710 amino acid residues from the N-terminal coding for the extracellular region, i.e., a protein comprising the EC1-EC5 domains. Because the domain nearest the N-terminal (EC1) of a cadherin molecule generally determines the binding specificity, or homophilic binding property, of the molecule (Nose et al., Cell 61:147, 1990), a protein molecule containing at least EC1 and lacking one or more of the other domains may be constructed and used. There may also be used a protein having at least 80%, preferably at least 85%, more preferably at least 90%, and most preferably at least 95% amino acid level homology with the aforementioned protein molecule, and exhibiting adhesion activity.

The recombinant protein mentioned above may also be produced as a fusion protein with another protein or peptide. For example, it may be, produced as a fusion protein with an immunoglobulin Fc region or with GST (Glutathione-S-Transferase) protein, MBP (Mannose-Binding Protein), avidin protein, His (oligo histidine) tag, HA (HemAgglutinin), Myc tag, VSV-G (Vesicular Stomatitis Virus Glycoprotein) tag or the like, and a Protein A/G column or a specific antibody column may be used for convenient and efficient purification of the recombinant protein. An Fc-fusion protein is particularly preferred for carrying out the invention because it has a greater ability to adsorb onto culture substrates made of materials such as polystyrene.

Numerous genes coding for immunoglobulin Fc regions have already been isolated and identified in mammals, including humans. Many of their nucleotide sequences have been reported, and for example, sequence data for nucleotide sequences containing human IgG1, IgG2, IgG3 and IgG4 Fc regions are accessible from public DNA databases such as NCBI, those sequences being registered respectively as Accession Nos.: AJ294730, AJ294731, AJ294732 and AJ294733. Thus, a person skilled in the art can design a primer or probe specific for the Fc region and use it in ordinary molecular biological techniques to obtain and use cDNA coding for the Fc region. In this case, the animal species and subtype of the gene coding for the Fc region of interest is not particularly limited, but preferably the gene codes for the Fc region of human IgG1 or IgG2 or murine IgG2a or IgG2b, which have strong binding affinity for Protein A/G. Methods for enhancing binding affinity for Protein A by introducing mutations into Fc regions are known (Nagaoka et al., Protein Eng. 16:243, 2003 (Non-patent document 7)), and Fc proteins with genetic modifications by such methods may also be used.

Examples of methods for producing recombinant proteins for E-cadherin, which is preferred for carrying out the invention have been published in the literature by the present inventors (Nagaoka et al., Biotechnol. Lett. 24:1857, 2002 (Non-patent document 6); Protein Eng. 16:243, 2003 (Non-patent document 7)).

Also, there is commercially available a purified recombinant protein produced by introducing into murine cells a fused gene obtained by linking cDNA having a sequence coding for the Fc region of human IgG and a His tag sequence to cDNA coding for the extracellular region of murine or human E-cadherin, and expressing the recombinant protein (Recombinant Human/Mouse E-cadherin-Fc Chimera; R&D systems, Genzyme Techne), which may be used as a mouse or human E-cadherin protein (E-cad-Fc protein).

For other cadherins such as N-cadherin, the fusion proteins thereof may also be produced in the same manner as in the E-cadherin.

As examples of culture substrates for cell culturing, there may be mentioned a dish (also referred to as a culture dish), a schale, a plate (for example, a 6-well, 24-well, 48-well, 96-well, 384-well or 9600-well microtiter plate, microplate, deep well plate and so on), a flask, a chamber slide, a tube, a cell factory, a roller bottle, a spinner flask, hollow fibers, microcarriers, beads and the like. These culture substrates may be made of inorganic materials such as glass, or of organic materials such as polystyrene, but it is preferable to use materials such as polystyrene, polyethylene or polypropylene that have high adsorption properties for proteins and peptides, or materials that have been treated by, for example, hydrophilic treatment or hydrophobic treatment for increased adsorption properties. Also preferred are sterilizable materials with high heat resistance and moisture resistance. As an example of such a preferred substrate, there may be mentioned a polystyrene dish and/or plate with no special cell culturing treatment (hereinafter referred to as "untreated polystyrene plate"), most commonly used for culturing of *E. coli* and the like, and such culture substrates are commercially available.

The method for immobilizing or coating N-cadherin or a protein homologous to N-cadherin, or a fusion protein comprising an entire or partial region of N-cadherin or a protein homologous to N-cadherin onto the solid phase surface of the culture substrate for carrying out the method disclosed by the invention may be a physical method such as adsorption or a chemical method such as covalent bonding, but an adsorption method is preferred for ease of execution. When the adhesion molecule is a protein or peptide molecule, or when it is a high molecular compound containing saccharide chains, the molecule can be easily adsorbed by contacting a solution of the molecule with the solid phase surface of a culture substrate such as a plate and removing the solvent after a prescribed period of time. More specifically, an adhesion molecule solution prepared using a solvent such as distilled water or PBS may be filtered and sterilized and then contacted with a culture substrate such as a plate, and it is allowed to stand for from a few hours to a full day/night period to obtain a cell culture substrate with the adhesion molecule immobilized or coated thereon. This is preferably used after rinsing several times with distilled water or PBS and replacing with a balanced saline solution such as PBS. Cadherins other than N-cadherin and fusion proteins can also be immobilized or coated in the same manner.

An artificial antigenic molecule is preferably added to or fused with the adhesion molecule beforehand because this will allow utilization of binding with antibodies specific for the antigenic molecule, and efficient attachment of the adhesion molecules on the substrate surface. In this case, the specific antibodies must be immobilized or coated on the culture substrate surface beforehand by a physical method such as adsorption or a chemical method such as covalent bonding. For example, for a recombinant protein obtained by fusing the IgG Fc region to the adhesion molecule, the antibody attached to the culture substrate beforehand may be one that specifically recognizes the IgG Fc region. For a recombinant protein obtained by fusing a protein or tag sequence peptide to the adhesion molecule, an antibody specific for the fused molecule may be attached to the culture substrate beforehand for use.

The two or more selected from the group consisting of a protein belonging to cadherin family and a fusion protein comprising an entire or partial region of a protein belonging to cadherin family may be used in combination for carrying out the invention. In such cases, solutions of each protein may be mixed and the mixed solution applied in the manner described above.

The concentration of the solution of a protein belonging to cadherin family or a fusion protein as described above must be appropriately considered based on the adsorption and/or affinity of the protein and the physical properties of the protein, but for a recombinant protein obtained by fusion of an Fc region with the extracellular region of E-cadherin or N-cadherin, the concentration is about 0.01-1000 µg/mL, preferably about 0.1-200 µg/mL, even more preferably 1-50 µg/mL and most preferably 3-20 µg/mL.

As described below, the cell culture substrate of the present invention can be suitably used for culturing of various pluripotent stem cells while maintaining their undifferentiated state, or for culturing for differentiation of pluripotent stem cells using added differentiation-inducing factor(s), or for culturing to select and concentrate desired cells from a group(s) of cells obtained by differentiating pluripotent stem cells.

[Cell Culturing Method]

The cell culturing method of the present invention is characterized by growing pluripotent stem cells using the cell culture substrate described above and a liquid medium while maintaining their undifferentiated state and pluripotency.

Unless otherwise specified, gene engineering methods employed in molecular biology and recombinant DNA technology, as well as common cell biology protocols and conventional techniques, may be employed for carrying out the invention, with reference to standard literature in the field. These include, for example, Molecular Cloning: A Laboratory Manual, 3rd Edition (Sambrook & Russell, Cold Spring Harbor Laboratory Press, 2001); Current Protocols in Molecular Biology (Ausubel et al. ed., John Wiley & Sons, 1987); Methods in Enzymology Series (Academic Press); PCR Protocols: Methods in Molecular Biology (Bartlett & Striling, eds., Humana Press, 2003); Animal Cell Culture: A Practical Approach, 3rd Edition (Masters ed., Oxford University Press, 2000); and Antibodies: A Laboratory Manual (Harlow et al. & Lane ed., Cold Spring Harbor Laboratory Press, 1987). The reagents and kits used for the cell culturing and cell biology experiments referred to throughout the present specification are available from commercial vendors such as Sigma, Aldrich, Invitrogen/GIBCO, Clontech and Stratagene.

Also, ordinary methods for cell culturing and development and cell biology experiments using the pluripotent stem cells may be carried out with reference to standard literature in the field. These include Guide to Techniques in Mouse Development (Wasserman et al. ed., Academic Press, 1993); Embryonic Stem Cell Differentiation in vitro (M. V. Wiles, Meth. Enzymol. 225:900, 1993); Manipulating the Mouse Embryo: A Laboratory Manual (Hogan et al. ed., Cold Spring Harbor Laboratory Press, 1994); and Embryonic Stem Cells (Turksen ed., Humana Press, 2002). The reagents and kits used for the cell culturing and development and cell biology experiments referred to throughout the present specification are available from commercial vendors such as Invitrogen/GIBCO and Sigma.

Standard protocols have already been established for generation, passaging and preservation of murine and human pluripotent stem cells, and these may be carried out using the pluripotent stem cells with reference to the literature mentioned above, as well as an abundance of other literature (Matsui et al., Cell 70:841, 1992; Thomson et al., U.S. Pat. No. 5,843,780; Thomson et al., Science 282:114, 1998; Shamblott et al., Proc. Natl. Acad. Sci. USA 95:13726, 1998; Shamblott et al., U.S. Pat. No. 6,090,622; Reubinoff et al., Nat. Biotech. 18:399, 2000; International Patent Publication No. WO00/27995). Methods are also known for establishing ES cells or ES-like cell lines for other animal species such as, for example, monkeys (Thomson et al., U.S. Pat. No. 5,843,780; Proc. Natl. Acad. Sci. USA, 92, 7844, 1996), rats (Iannaccone et al., Dev. Biol. 163:288, 1994; Loring et al., International Patent Publication No. WO99/27076), chickens (Pain et al., Development 122:2339, 1996; U.S. Pat. No. 5,340,740; U.S. Pat. No. 5,656,479), pigs (Wheeler et al., Reprod. Fertil. Dev. 6:563, 1994; Shim et al., Biol. Reprod. 57:1089, 1997) and the like, and the ES cells used for the invention may be prepared according to methods described for each.

ES cells are pluripotent stem cells isolated as an aggregate of undifferentiated stem cells by extracting the cell mass in the interior of the blastocyst-stage embryo, known as an inner cell mass, and transferring it to in vitro culture, with repeated detachment and passaging of the cell mass. As murine ES cells, there are known various lines including E14, D3, CCE, R1, J1, EB3 and the like, some of which may be obtained from the American Type Culture Collection, Cell & Molecular Technologies or Thromb-X. Currently, 50 human ES cell lines have been established throughout the world, and 20 different lines are registered at the U.S. National Institutes of Health (NIH) (http://stemcells.nih.gov/registry/index.asp). Some of these may be obtained from ES Cell International or the Wisconsin Alumni Research Foundation.

ES cell lines are usually established by culturing of early embryos, but ES cells can also be produced from early embryos obtained by nuclear transfer of somatic cell nuclei (Munsie et al., Curr. Biol. 10:989, 2000; Wakayama et al., Science 292:740, 2001; Hwang et al., Science 303: 1669, 2004). There have also been proposed methods for generating ES cells from blastocyst-stage embryo-like cellular structures obtained by transferring cell nuclei of desired animals into another species of oocytes or denucleated oocytes divided into several portions (known as cytoplasts or ooplastoids) (International Patent Publication Nos. WO99/45100; WO01/46401; WO01/96532; U.S. Pregnant Publication Ser. Nos. 02/90722; 02/194,637). There have also been reported, for example, an attempt to produce ES cells from a parthenogenetic embryo developed to the same stage as the blastocyst-stage (U.S. Pregnant Publication No. 02/168763; Vrana K et al., Proc. Natl. Acad. Sci. USA 100:11911-6), and a method of fusing ES cells with somatic cells to produce ES cells having the genetic information of the somatic cell nuclei (International Patent Publication No. WO00/49137; Tada et al., Curr. Biol. 11:1553, 2001). The ES cells used for the invention include ES cells produced by such methods and ES cells whose chromosomal DNA has been modified by genetic engineering techniques.

EG cells are cells produced by stimulating fetal germ cells known as primordial germ cells on feeder cells such as MEF cells, STO cells or Sl/Sl$^4$-m220 cells with a chemical agent such as LIF, bFGF/FGF-2 or forskolin in the same manner as in ES cells (Matsui et al., Cell, 70:841, 1992; Koshimizu et al., Development, 122:1235, 1996), and their properties are very similar to those of ES cells (Thomson & Odorico, Trends Biotechnol., 18:53, 2000). As with ES cells, EG cells produced by fusing EG cells with somatic cells (Tada et al., EMBO J., 16:6510, 1997; Andrew et al.) and EG cells whose chromosomal DNA has been modified by genetic engineering techniques may also be used for the method of the invention.

iPS cells (induced pluripotent stem cells) are cells having pluripotency which are obtained by reprogramming of somatic cells. iPS cells can be produced by the methods as described in the above Patent Documents 3, 4 and 5. In addition to the methods described in the above Patent Documents, many modified methods for producing iPS cells have been known. International Patent Publication No. WO2007/069666 describes a nuclear reprogramming factor for somatic cells comprising gene products of an Oct family gene, a Klf family gene and an Myc family gene; a nuclear reprogramming factor for somatic cells comprising gene products of an Oct family gene, a Klf family gene, a Sox family gene and an Myc family gene; and a method for producing induced pluripotent stem cells by nuclear reprogramming of somatic cells, which comprises a step of contacting the nuclear reprogramming factor as mentioned above with the somatic cells. Further, methods in which one or more of the reprogramming factors as mentioned above is/are not used and other factor(s) is/are used, and methods in which other substance(s) and/or gene(s) is/are used instead of or in addition to the reprogramming factors have been known. The iPS cells used for the present invention may be produced any method, as long as they fall within the definition of iPS cells.

The iPS cells to be used in the present invention may be produced by reprogramming of somatic cells. The type of the somatic cells used here is not particularly restricted, and any somatic cells can be used. Somatic cells include all cells composing a living body except germ cells, and may be differentiated somatic cells or undifferentiated stem cells. The origin of the somatic cells is not particularly restricted, and may be any of mammals, birds, fishes, reptiles and amphibians, but it is preferably a mammal (for example, a rodent such as mouse or a primate such as human), especially preferably a mouse or human. When human somatic cells are used, any of fetal somatic cells, neonatal somatic cells or adult somatic cells can be used.

Moreover, pluripotent stem cells are not limited to ES cells, EG cells or iPS cells, but include all pluripotent stem cells derived from a mammalian embryo or fetus, umbilical cord, or adult tissue or blood, such as adult organs or bone marrow, and having ES/EG cell-like features. For example, ES-like cells obtained by culturing germ cells under special culturing conditions exhibit features extremely similar to ES/EG cells (Kanatsu-Shinohara et al., Cell, 119:1001, 2004), and may be used as pluripotent stem cells. As another example, there may be mentioned multipotent adult progenitor/stem cells (MAPC) isolated from bone marrow cells and having the potential to differentiate into all three germ layers. Moreover, pluripotent stem cells obtained by culturing root sheath cells or keratinocytes (International Patent Publication No. WO02/51980), intestinal epithelial cells (International Patent Publication No. WO02/57430) or inner ear cells (Li et al., Nature Med., 9:1293, 2003) under special culturing conditions, and pluripotent stem cells produced by treatment of blood mononuclear cells (or stem cells contained in their cell fraction) with M-CSF (Macrophage-Colony Stimulating Factor)+PMA (phorbol 12-myristate 13-acetate) (Zhao et al., Proc. Natl. Acad. Sci. USA, 100: 2426, 2003) or CR3/43 antibody (Abuljadayel, Curr. Med. Res. Opinion, 19:355, 2003), are also all included as long as their features resemble those of ES/EG cells. In this case, features resembling ES/EG cells may be defined as cell biology properties unique to ES/EG cells, such as the presence of surface (antigenic) markers specific to the cells and expression of genes specific to the cells, as well as teratoma-forming potential and chimeric mouse-forming potential.

The pluripotent stem cells used to carry out the invention are seeded on the cell culture substrate of the present invention as described above. The culturing method and culturing conditions for the pluripotent stem cells may be an ordinary culturing method and culturing conditions for pluripotent stem cells, except for using the culture substrate described above. Ordinary culturing methods and culturing conditions for pluripotent stem cells are described in the literature mentioned above, and specifically, Guide to Techniques in Mouse Development (Wasserman et al. eds., Academic Press, 1993); Embryonic Stem Cell Differentiation in vitro (M. V. Wiles, Meth. Enzymol., 225:900, 1993); Manipulating the Mouse Embryo: A laboratory manual (Hogan et al. eds., Cold Spring Harbor Laboratory Press, 1994); Embryonic Stem Cells (Turksen ed., Humana Press, 2002), as well as other sources (Matsui et al., Cell, 70:841, 1992; Thomson et al., U.S. Pat. No. 5,843,780; Thomson et al., Science, 282:114, 1998; Shamblott et al., Proc. Natl. Acad. Sci. USA, 95:13726, 1998; Shamblott et al., U.S. Pat. No. 6,090,622; Reubinoff et al., Nat. Biotech., 18:399, 2000; and International Patent Publication No. WO00/27995), although there is no particular restriction to these.

The liquid medium used for the culturing of the pluripotent stem cells may be any one that can be employed in conventional methods of passaging pluripotent stem cells. As specific examples, there may be mentioned Dulbecco's Modified Eagle's Medium (DMEM), Glasgow Minimum Essential Medium (GMEM), RPMI1640 medium and the like, usually with addition of about 2 mM of glutamine and/or about 100 µM of 2-mercaptoethanol. There may also be used KnockOut DMEM (Invitrogen), ES cell-qualified DMEM (Cell & Molecular Technologies) and TX-WES (Thromb-X), which are commercially available as ES cell culturing media. Such media preferably contain FBS added to about 5-25%, but they may also be serum-free media, substituted with, for example, 15-20% KnockOut Serum Replacement (Invitrogen). MEF cell culture supernatant or medium containing added bFGF/FGF-2, SCF and the like may also be used, and detailed procedures therefor are publicly known (Xu et al., Nature Biotech. 19:971, 2001; International Patent Publication No. WO01/51616; International Patent Publication No. WO03/020920; Amit et al., Biol. Reprod., 70:837, 2004).

The liquid medium for culturing of the pluripotent stem cells also preferably has substances and factors added thereto which help maintain the undifferentiated state of the pluripotent stem cells. The specific substances and factors are not particularly restricted, but LIF is preferred for murine ES/EG cells. LIF is a protein factor that is publicly known from the published literature (Smith & Hooper, Dev. Biol. 121:1, 1987; Smith et al., Nature 336:688, 1988; Rathjen et al., Genes Dev. 4:2308, 1990), as well as by Access Nos. X13967 (human LIF), X06381 (murine LIF) and NM_022196 (rat LIF), and its recombinant proteins can be obtained, for example, under the trade name of ESGRO (Chemicon). Addition of GSK-3 inhibitor to the culture medium can efficiently maintain the undifferentiated state of murine and human ES cells without addition of other growth factors or bioactive factors (Sato et al., Nature Med. 10:55, 2004). In this case, any substance having activity of inhibiting GSK-3 activity may be used, and there may be mentioned, for example, the Wnt family of molecules (Manoukian & Woodgett, Adv. Cancer Res. 84:203, 2002; Doble & Woodgett, J. Cell Sci. 116:1175, 2003).

By seeding pluripotent stem cells that have been maintained through passaging by conventional methods on culture substrate prepared by the method described above and culturing with the aforementioned culturing conditions and method for carrying out the invention, it is possible to accomplish passaging with the cells in a dispersed state, while maintaining the original undifferentiated state of the cells. Since the pluripotent stem cells cultured in this state are not physically inhibited during cell division, and/or the cell growth-inhibiting mechanisms mediated by intercellular contact do not function, and/or cell survival is increased and the dead cell count is decreased, significant cell proliferation and growth is observed. In the case of culturing of murine ES cells by the method of the invention, as one example, it is possible to achieve a proliferation rate of at least 1.25 times, preferably at least 1.5 times and more preferably at least 2 times compared to culturing by a conventional method. Passaging to about 4 generations under these conditions allows recovery of at least 3 times, and preferably at least 10 times, the number of cells recovered by conventional methods. The proliferation rate may be indicated by indices such as the cell count increase rate or doubling speed per unit of time, and the methods of measurement and calculation used may be any publicly known methods employed for common cell experiments.

As explained above, the state of undifferentiation of pluripotent stem cells means that the pluripotent stem cells are capable of prolonged or virtually indefinite proliferation and exhibit normal karyotype (chromosomes), while having the capacity to differentiate into all three germ layers under the appropriate conditions. Also, they preferably have at least one of the other properties of pluripotent stem cells such as telomerase activity maintenance, teratoma formation, or ability to form chimeras. Methods of examining cell character and properties may be easily carried out using established standard protocols with reference to the literature cited above such as, for example, Guide to Techniques in Mouse Development (Wasserman et al. eds., Academic Press, 1993); Embryonic Stem Cell Differentiation in vitro (M. V. Wiles, Meth. Enzymol. 225:900, 1993); Manipulating the Mouse Embryo: A Laboratory Manual (Hogan et al. eds., Cold Spring Harbor Laboratory Press, 1994); or Embryonic Stem Cells (Turksen ed., Humana Press, 2002), but there is no particular restriction to these methods.

Pluripotent stem cells in an undifferentiated state may be defined as cells for which at least one and preferably more marker molecules can be confirmed by at least one, and preferably more than one, of the methods described below. Expression of various markers specific to undifferentiated pluripotent stem cells is detected by conventional biochemical or immunochemical methods. Although there are no particular restrictions on the method employed, immunochemical methods such as immunohistological staining or immunoblot analysis are preferred. There may be utilized, in such methods, marker-specific polyclonal antibodies or monoclonal antibodies that bind to undifferentiated pluripotent stem cells. Antibodies that target individual specific markers are commercially available and may be conveniently used. Specific markers for undifferentiated pluripotent stem cells include ALP activity and Oct-3/4 or Rex-1/

Zfp42 gene product expression. Various antigenic molecules may also be used, which include the undifferentiation markers SSEA-1 for murine ES cells, SSEA-3 for human ES cells, or SSEA-4, TRA-1-60, TRA-1-81 gCTM-2 and the like. Expression of them is reduced or eliminated upon differentiation of ES cells.

Alternatively, expression of undifferentiated pluripotent stem cells markers can be confirmed by molecular biological methods employed often in the prior art for amplification, detection and analysis of mRNA coding for desired marker proteins, such as reverse transcriptase polymerase chain reaction (RT-PCR) or hybridization analysis, without regard to the particular method. Nucleic acid sequences for genes coding for marker proteins specific to undifferentiated pluripotent stem cells (for example, Oct-3/4, Rex-1/Zfp42 or Nanog) are known, and marker-specific sequences necessary as primers or probes can be easily determined working from public databases such as NCBI.

[Differentiation Induction Method]

The method for inducing differentiation of pluripotent stem cells of the present invention is characterized by differentiating pluripotent stem cells using the cell culture substrate of the present invention as described above and a liquid medium containing a differentiation-inducing factor(s).

The culturing method and culturing conditions for inducing differentiation of the pluripotent stem cells may be an ordinary culturing method and culturing conditions for inducing differentiation of pluripotent stem cells, except for using the cell culture substrate of the present invention as described above. For the liquid medium, those which are the same as described above may be used.

Differentiation-inducing factors (also referred to as growth factors) are compounds, such as peptides, hormones, cytokines, proteins and glycoproteins, that are to be added to the medium in order to induce differentiation of pluripotent stem cells, and various differentiation-inducing factors are used depending on the type and/or differentiation stage of the cells desired to be differentiated. In the present invention, a publicly known differentiation-inducing factor(s) depending on the desired cells may be added to the liquid medium according to a known method or protocol.

For example, taking as an example the differentiation into hepatocytes, hepatocytes can be obtained by differentiating ES cells into mesendoderm (mesendodermal cells), definitive endoderm (endodermal cells), hepatic progenitor cells and hepatocytes in this order. For differentiation into hepatocytes, a differentiation-inducing factor(s) such as Activin A, Nodal, bFGF (basic fibroblast growth factor), HGF (hepatocyte growth factor), OSM (Oncostatin M), DEX (dexamthasone), EGF (epidermal growth factor) and/or TGF-α (transforming growth factor-α) is/are used, but a factor(s) other than these may be used according to a publicly known technique described in literature. Also in cases of cells other than hepatocytes, differentiation into the cells can be achieved by using a differentiation-inducing factor(s) necessary for the differentiation.

An example of a scheme for inducing differentiation into neural cells is shown in FIG. 5(A).

Since cell adhesion by a protein belonging to cadherin family is $Ca^{2+}$-dependent, it is preferred to use a chelating agent in a method of detaching the hepatocytes after the differentiation induction from the cell culture substrate. As the chelating agent, any publicly known chelating agents may be used, but one that has no negative effect on the cells is preferable.

Use as Gene Transfer Method into Pluripotent Stem Cells

According to another mode of the invention, the method disclosed by the invention may be used as a method for efficient transfer of a desired exogenous gene into pluripotent stem cells. There are no particular restrictions on the exogenous gene to be transferred, and for example, it may be for a natural protein such as a growth factor or receptor, an enzyme, a transcription factor or the like, or an artificial protein generated by modification using a genetic engineering method. The transferred gene may also be functional RNA such as a ribozyme or siRNA. The exogenous gene may even be a marker gene for evaluation of gene transfer efficiency or expression stability, such as a gene coding for GFP (Green Fluorescent Protein) or β-galactosidase, luciferase or the like.

As one preferred mode, the exogenous gene to be transferred is linked to a nucleic acid sequence that allows transcription and expression of the gene, i.e., a promoter sequence, under control of the promoter in a form allowing its transcription and expression. In such cases the gene is also preferably linked to a polyA signal sequence. As promoters that allow transcription and expression of exogenous genes in pluripotent stem cells, there may be mentioned promoters from viruses such as SV40 virus, CMV or Rous sarcoma virus, or β-actin promoter, EFla promoter or the like. Depending on the purpose, there may also be used a nucleic acid sequence allowing transcription or expression of a specific gene in certain cell/tissue types or in cells of a given stage of differentiation, i.e., a cell/tissue-specific promoter sequence or differentiation stage-specific promoter, or Pol. III promoter for RNA expression. These promoter sequences may be utilized from public DNA databases such as NCBI, and ordinary molecular biological techniques may be employed to construct gene vectors comprising desired gene sequences. Vectors for these promoters may be obtained from Invitrogen, Promega, Ambion and elsewhere.

The method for introducing the gene (vector) is not particularly restricted, and there may be mentioned, for example, transfection methods using calcium phosphate or DEAE-dextran. Transfection methods for cell targets of the gene transfer can also be applied using lipid preparations that can be taken up into the cells and have low cytotoxicity, such as LipofectAMINE (Invitrogen), Superfect (Qiagen) or DOTMA (Roche), to form liposome-nucleic acid complexes containing the target gene. Alternatively, the gene of interest may be incorporated into a viral vector such as a retrovirus or adenovirus and the recombinant virus used to infect the cells. In this case, the viral vector is a re-construct of the nucleic acid sequence of full-length or partially deficient or mutated viral DNA or RNA, with the gene of interest incorporated in an expressible manner.

Use of Pluripotent Stem Cells Grown by Method of the Invention

The pluripotent stem cells that have been grown by the growing method according to the invention may then be obtained efficiently and in large amounts as pluripotent stem cells maintaining their undifferentiated state, using publicly known cell recovery methods. The gene transfer method of the invention allows efficient and high-yield production of pluripotent stem cells having the desired gene transferred and expressed therein. The pluripotent stem cells obtained in this manner will hereinafter be referred to as "pluripotent stem cells prepared according to the invention".

As methods of recovering pluripotent stem cells there may be mentioned methods using publicly known enzyme treatment, which are ordinarily employed for passaging of pluripotent stem cells. As a specific example, there may be mentioned a method wherein the medium is removed from a culturing vessel in which pluripotent stem cells have been cultured, PBS is used for rinsing several times, preferably 2-3 times, a solution containing an appropriate protease (for example, a solution containing a protease such as trypsin or dispase) is added, culturing is carried out at 37° C. for an appropriate period, preferably about 1-20 minutes and more preferably 3-10 minutes, and then the mixture is suspended in an appropriate solution such as the aforementioned ES cell culturing medium to obtain single cells. Non enzymatic methods may also be used, and for example, there may be mentioned a method wherein the medium is removed from a culturing vessel in which pluripotent stem cells have been cultured, PBS is used for rinsing several times, preferably 2-3 times, an ethylenediamine tetraacetate (EDTA) solution is added to a final concentration of 0.01-100 mM, preferably 0.1-50 mM and more preferably 1-10 mM, for treatment at 37° C. for an appropriate time, preferably about 1-60 minutes and more preferably 10-30 minutes for detachment of the cells, and then the mixture is suspended in an appropriate solution such as the aforementioned ES cell culturing medium to obtain individual cells. The same method may also be carried out using ethyleneglycol bis(2-aminoethylether)tetraacetate (EGTA) instead of EDTA.

The present invention also provides differentiated cells produced by appropriate differentiation-inducing treatment from pluripotent stem cells prepared according to the invention. The differentiated cells are not particularly restricted as long as they are of a cell type whose differentiation can generally be induced from pluripotent stem cells. Specifically, there may be mentioned ectodermal cells or ectoderm-derived cells, mesodermal cells or mesoderm-derived cells, endodermal cells or endoderm-derived cells, and the like.

Ectoderm-derived cells are cells composing tissues and organs such as neural tissue, the pineal body, the adrenal medulla, plastids and epidermal tissue, but they are not limited to these. Mesoderm-derived cells are cells composing tissues and organs such as muscle tissue, connective tissue, bone tissue, cartilage tissue, cardiac tissue, vascular tissue, blood tissue, dermal tissue, urinary organs and reproductive organs, but they are not limited to these. Endoderm-derived cells are cells composing tissues and organs such as digestive tract tissue, respiratory organs, or thymus, thyroid, parathyroid, bladder, middle ear, liver and pancreas tissue, but they are not limited to these.

The pluripotent stem cells prepared according to the invention and/or differentiated cells prepared from such cells are useful for pharmacological evaluation or activity evaluation of various physiologically active substances (such as drugs) or novel gene products of unknown function. For example, they may be utilized for screening of substances and drugs involved with functional regulation of pluripotent stem cells or various differentiated cells, and/or substances or drugs with toxicity or inhibitory action on pluripotent stem cells or various differentiated cells. Currently, very few screening methods have been established using human cells, and differentiated cells derived from pluripotent stem cells prepared according to the invention are useful cell sources for conducting such screening methods.

The invention also relates to a method of generating a chimeric embryos or chimeric animals using pluripotent stem cells prepared by the method disclosed by the invention, and to the generated chimeric embryos and chimeric animals. Standard protocols have already been established for generating chimeric embryos and chimeric animals, and they can be easily generated with reference to, for example, Manipulating the Mouse Embryo: A Laboratory Manual (Hogan et al. eds., Cold Spring Harbor Laboratory Press, 1994), though there is no particular limitation to this reference.

EXAMPLES

The present invention will be described below in more detail with reference to Examples, but the present invention is not limited to these Examples in any way.

Experiments carried out in the Examples of the present invention are as follows.

<Media>

A feeder-dependent mES cell line (ST1) and Nanog-GFP expressing miPS cell line (APS0001 iPS-MEF-Ng-20D-17) were routinely cultured on murine embryonic fibroblast (MEF) cells in 35 mm culture dishes coated with gelatin in a humidified atmosphere of 5% $CO_2$ at 37° C. The ST1 cells were maintained in Dulbecco's Modified Eagle's Medium (DMEM, Sigma-Aldrich), supplemented with 20% (v/v) fetal bovine serum (FBS), 1 mM sodium pyruvate (nacalai tesque), 1 mM L-glutamine (Millipore), 1% nonessential amino acids (NEAAs; Gibco, Invitrogen), 0.1 mM 2-mercaptoethanol (Sigma Chemical) and 1000 units/ml LIF. The miPS cells were cultured in a medium supplemented with DMEM (high glucose without pyruvate; Sigma), 15% FBS, 0.1 mM NEAAs, 0.1 mM 2-mercaptoethanol and 1000 units/ml LIF. All media contained 50 µg/ml penicillin and 50 µg/ml streptomycin (nacalai tesque). The mES cells and the miPS cells were passaged every three days with medium replacement. A mouse embryonic carcinoma cell line (P19) and a feeder-independent mES cell line (EB3 cell line) were used as controls in intercellular adhesion analysis and mRNA expression analysis. The culturing conditions for the P19 and EB3 cells were as described in earlier literature (Yue X S et al., Biomaterials, 2010; 31:5287-96, and Hague A et al., Biomaterials, 2011; 32: 2032-42).

<Preparation of Natural and Artificial Substrata>

In order to prepare gelatinized surfaces, tissue culture dishes were treated with 0.1% gelatin for 30 minutes at 37° C. Expression and purification of E-cadherin-Fc (E-cad-Fc) and N-cadherin-Fc (N-cad-Fc) fusion proteins, and immobilization of these fusion proteins onto polystyrene culture dishes were carried out as described in earlier literature (Yue X S et al., Biomaterials, 2010; 31:5287-96, and Nagaoka M et al., Plos one, 2006; 1. e15). Briefly, in order to prepare E-cad-Fc- or N-cad-Fc-coated surfaces, the purified fusion proteins thereof were diluted into 10 µg/ml; the diluted solutions were separately added to non-treated polystyrene culture dishes; and the dishes were incubated at 37° C. for 1 hour. In order to prepare E-cad-Fc and N-cad-Fc co-immobilized substrata, the optimized concentration of E-cad-Fc (5 µg/ml) and N-cad-Fc (5 µg/ml) were added to a non-treated polystyrene culture dish, and the dish was incubated at 37° C. for 1 hour. The polystyrene surfaces after the immobilization were washed once with PBS, and incubated with 0.25% BSA/PBS solution at 37° C. for 2 hours to inhibit nonspecific adsorption of the cells thereon.

<Cell Adhesion and Proliferation Assay>

The adsorption of the mES cells and the miPS cells onto these extracellular matrices (ECMs), and their proliferation thereon were measured by MTT assay. Briefly, 24-well microplates were treated with each of these adhesion molecules at 37° C. for 1 hour to coat with them. Onto these plates containing the media for the ES cells or the iPS cells, the cells at confluent density ($1 \times 10^4$ cells/well) were seeded at different time points. Four hours later, the media and non-adsorbed cells were removed, and the plates were washed with DMEM basal medium. Then, culturing was carried out in the undifferentiating media. To each well, 5 mg/ml MTT solution was added, and the cells were cultured at 37° C. for 4 hours. Their adsorption on the plates was measured by a microplate reader with the wavelength of 570 nm using a reference wavelength of 630 nm.

<Alkaline Phosphatase Assay>

The alkaline phosphatase (AP) activity of the mES cells and the miPS cells that had been cultured in the undifferentiating media for 4 days on 12-well plates coated with the adhesion molecules was measured according to the instructions attached to the measuring kit product (Sigma, Leukocyte Alkaline Phosphatase Kit, 85L3R).

<Flow Cytometry>

Recovery of cultured miPS cells was carried out using Accutase and the cells were analyzed. The separated $1 \times 10^6$ cells/ml were suspended in cold PBS and centrifuged to remove the enzyme. Then, analysis of Nanog expressing cells was carried out using a flow cytometer (Guava Technologies, Millipore).

<Induction of Differentiation>

The compositions of basal differentiation media for the ES cells or the iPS cells were identical to those of the media described above except that Grasgow minimum essential medium (GMEM, Sigma), stage-specific differentiation-inducing factors and 10% (v/v) knockout serum replacement (KSR, Invitrogen) were added thereto, while DMEM, LIF and FBS were omitted. Before starting induction of differentiation, culturing of the mES cells and the miPS cells on plates that had been coated with 10 µg/ml E-cad-Fc was carried out to remove the feeder cells. For inducing monolayer differentiation, the mES cells and the miPS cells were seeded onto the plate surfaces coated with E-cad-Fc, the plate surfaces coated with N-cad-Fc or the plate surfaces co-immobilized with E-cad-Fc and N-cad-Fc. The cells were cultured in the undifferentiating media for 24 hours before induction of differentiation. Induction of neural differentiation using the monolayer protocol was carried out by culturing for 5 days in KSR differentiation media supplemented with 10 ng/ml DKK-1 and 500 ng/ml Lefty-A. From days 6-12, the cells were cultured in the basal differentiation media supplemented with basic fibroblast growth factor (bFGF, 20 ng/ml, Promega). The media were replaced every two days. Observation of their growth and morphological changes was performed daily. The differentiation was confirmed through observation of their axon formation, RT-PCR, and immunostaining.

Spontaneous differentiation into embryoid bodies (EBs) was carried out using a hanging drop method. Briefly, the cells on the E-cad-Fc-coated culture dishes were separated using Accutase and diluted with the undifferentiating media for the ES or iPS cells which did not contain LIF. Thereafter, 20 µl drops containing 600 cells were placed on the inside of polystyrene petri dish lids. On day 3 and day 5, 5 drops containing embryoid bodies were transferred to 35 mm culture dishes coated with 0.1% gelatin, and cultured in the absence of LIF for one more day. On day 4 and day 6, the EBs were collected for mRNA expression analysis. For neural differentiation using the hanging drop method, the same protocol was used except that the neural differentiation media were used as the drops during the period from day 1 to day 5 after starting the induction of differentiation. The EBs were then transferred to gelatin-coated culture dishes, and cultured in the presence of bFGF for another 5 days. Observation of their cell growth and morphological changes was performed daily. The cells were recovered at different time points after the start of the differentiation induction, and analysis using stage-specific markers was carried out.

<Immunofluorescent Staining>

The cells were fixed with Mildform 20 N (8% formaldehyde) for 15 minutes and permeabilized using 0.2% Triton X-100 (nacalai tesque) for 5 minutes. The fixed cells were blocked with Blocking one solution (nacalai tesque) for 1 hour. As primary antibodies, mouse anti-E-cadherin antibody (BD Transduction Laboratories), rabbit anti-mouse N-cadherin antibody (H-63, Santa Cruz Biotechnology), anti-mouse SSEA1 antibody (Santa Cruz Biotechnology), rabbit anti-human Oct3/4 antibody (Santa Cruz Biotechnology), rabbit anti-human Nestin antibody (IBL Ltd., Japan), mouse anti-neuron specific βIII-tubulin antibody (Tuj-1, R&D Systems, Inc.), and mouse anti-GFAP antibody (GAS, Cell Signaling) were used. As secondary antibodies, goat anti-mouse IgG F(ab')$_2$-TRITC antibody (Santa Cruz), anti-rabbit IgG F(ab')$_2$ Alexa Fluor 555-conjugated antibody (Cell Signaling), anti-mouse Cy3 F(ab')$_2$ secondary antibody conjugated with Alexa fluorophore (Invitrogen), and anti-mouse IgG F(ab')$_2$ Alexa Fluor 488-conjugated antibody (Invitrogen) were used.

<RT-PCR>

Total RNA was extracted using Trizol reagent (Invitrogen). RNA was reverse-transcribed into cDNA with an oligo-T primer using Moloney murine leukemia virus (M-MLV) reverse transcriptase (Invitrogen). PCR was performed using Ex Taq polymerase (Takara) and a PCR buffer containing 0.2 mM dNTPs. The primers and PCR conditions thereof are shown in Table 1. The amounts of RNAs for each marker were calculated from the fluorescent signals of the PCR products using ImageQuant image analysis software (ver. 5.2, Molecular Dynamics).

TABLE 1

(SEQ ID NOS 1-38, respectively, in order of appearance)
List of primer sequences used in this study.

| Genes analyzed | Forward primer (5'-3') | Reverse primer (5'-3') | Annealing temp. (° C.) |
|---|---|---|---|
| Primitive | | | |
| Nanog | GAGGAAGCATCGAATTCTGG' | AAGTTATGGAGCGGAGCAGC' | 58 |
| Neural | | | |
| N-cadherin | CAGTCTTACCGAAGGATGTGC | ATCAGCTCTCGATCCAGAGG | 58 |
| Sox1 | CCTCGGATCTCTGGTCAAGT | TACAGAGCCGGCAGTCATAC | 58 |
| Sox2 | GAACGCCTTCATGGTATGG | AGCCGTTCATGTAGGTCTGC | 55 |
| Nestin | GCTACATACAGGACTCTGCTG | AAACTCTAGACTCACTGGATTCT | 55 |

TABLE 1 -continued (SEQ ID NOS 1-38, respectively, in order of appearance)
List of primer sequences used in this study.

| Genes analyzed | Forward primer (5'-3') | Reverse primer (5'-3') | Annealing temp. (° C.) |
|---|---|---|---|
| Ngn1 | CGATCCCCTTTTCTCCTTTC | TGCAGCAACCTAACAAGTGG | 55 |
| MAP2 | TCAGACTTCCACCGAGCAG | AGGGGAAAGATCATGGCCC | 55 |
| BLBP | GGGTAAGACCCCGAGTTCCTC | ATCACCACTTTGCCACCTTC | 58 |
| βIII-tubulin | AGCGATGAGCACGGCATAG | CAGGTTCCAAGTCCACCAGA | 55 |
| GFAP | GGAGAGGGACAACTTTGCAC | GCTCTAGGGACTCGTTCGTG | 55 |
| Pax6 | TGCCCTTCCATCTTTGCTTG | TCTGCCCGTTCAACATCCTTAG | 58 |
| TH | TCCTGCACTCCCGCTCAGAG | CCAAGAGCAGCCCATCAAAGG | 58 |
| Mesendoderm | | | |
| Brachyury | ATGCCAAAGAAAGAAACGAC | AGAGGCTGTAGAACAGGATT | 55 |
| Goosecoid | ATGCTGCCCTACATGAACGT | CAGTCCTGGGCCTGTACATT | 55 |
| Endoderm | | | |
| Foxa2 | TATTGGCTGCAGCTAAGCGG | GACTCGGACTCAGGTGAGGT | 55 |
| Sox17 | TTTGTGTATAAGCCCGAGATGG | AAGATTGAGAAAACACGCATGAC | 55 |
| Gata6 | ACCTTATGGCGTAGAAATGCTGAGGGTG | CTGAATACTTGAGGTCACTGTTCTCGGG | 60 |
| Mesoderm | | | |
| Gata1 | CACCATCAGGTTCCACAGG | TTGAGGCAGGGTAGAGTGC | 55 |
| House keeping | | | |
| β-actin | CCTAAGGCCAACCGTGAAAAG | TCTTCATGGTGCTAGGAGCCA | 55 |

<Western Blot>

Total protein in the cells was extracted with lysis buffer (10 mM Tris-HCl, 150 mM sodium chloride, 1% Nonidet P-40, 10 mM EDTA, and protease inhibitor cocktail, pH 7.4), and the cell lysates were centrifuged at 15000×g for 15 minutes at 4° C. The samples were separated by electrophoresis using 7.5% polyacrylamide gels, and transferred to polyvinylidene difluoride membranes (Immobilon-P, Millipore). As primary antibodies, mouse anti-E-cadherin antibody (BD Transduction Laboratories), rabbit anti-human N-cadherin antibody (Santa Cruz Biotechnology), mouse anti-FAK antibody (BD Transduction Laboratories), mouse anti-pFAK antibody (BD Transduction Laboratories), and mouse anti-β-actin antibody (Sigma) were used. The membranes were reacted with horseradish peroxidase (HRP)-conjugated secondary antibody (1:10000 dilution, Jackson ImmunoResearch Laboratories) for 1 hour. The HRP activity was measured using Immobilon Western detection reagents (Millipore) according to the instructions attached to the product.

<Statistical Analyses>

The data are presented as the mean±standard deviation (SD). Statistical analyses were performed with Student's t-test for paired samples. A p-value less than 0.05 was considered statistically significant.

(Results)

<Pluripotency of Feeder-Dependent Murine ES Cells and iPS Cells>

Figure 1:
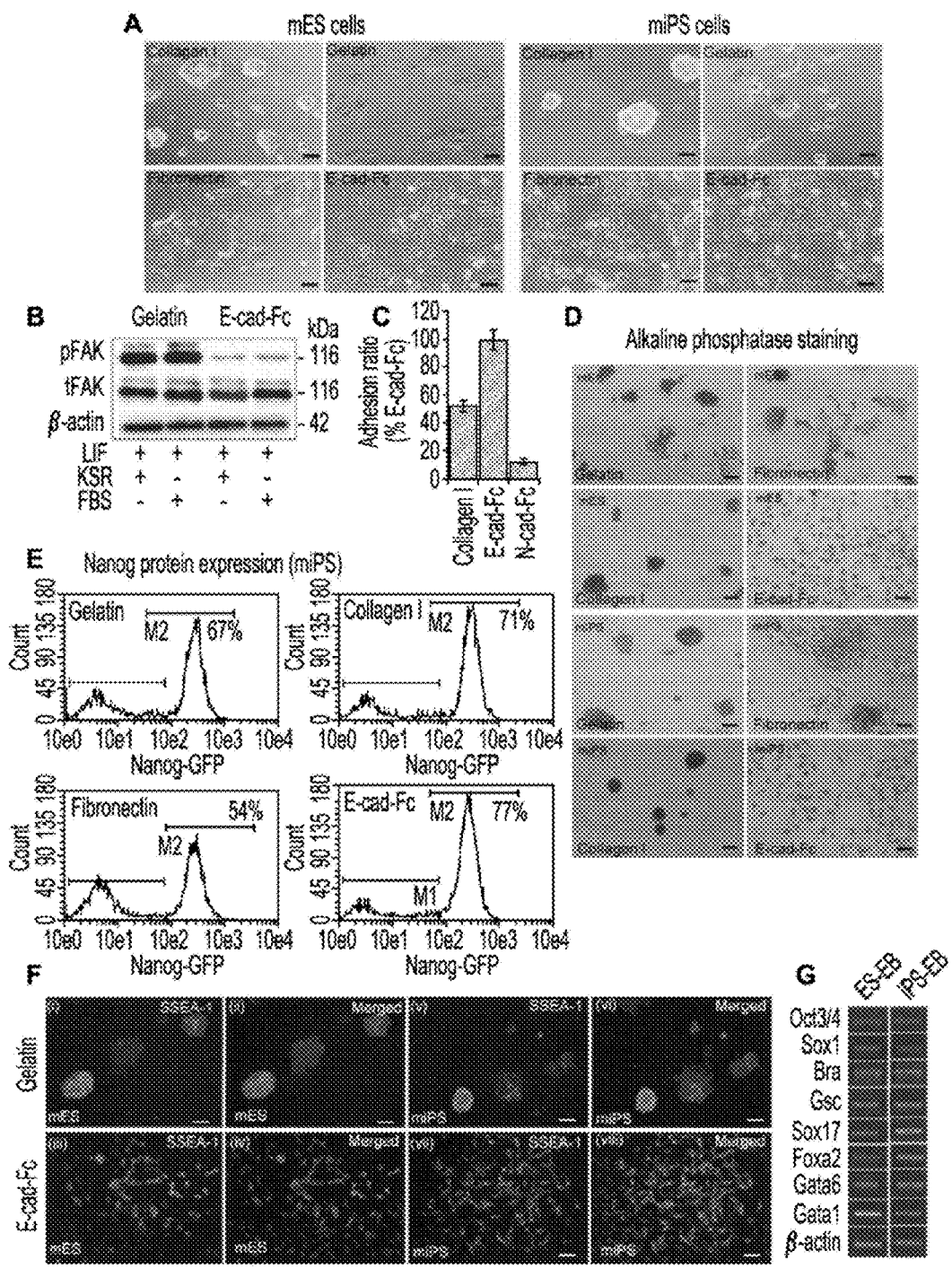
FIG. 1 shows the effect of cadherin-based artificial extracellular matrices (ECMs) on murine ES cells and murine iPS cells.
(A) Photographs showing the states of the cell morphology and colony formation after culturing the mES cells and the miPS cells on various extracellular matrices. The feeder-dependent ES cells and iPS cells on 0.018% type I collagen (upper left) formed spherical colonies. The ES cells and the iPS cells on 5 μg/ml fibronectin (lower left) or 0.1% gelatin (upper right) spread out like differentiated cells. The cells on 10 μg/ml E-cadherin substrate (lower right) dispersed into single cells.

First, the effect of the E-cadherin substrata on the feeder-dependent mES cells (ST1) and miPS cells was confirmed prior to the induction of neural differentiation. The culturing of the mES cells and the miPS cells on various ECMs led to a variety of changes in the cell morphologies and shapes (FIG. 1A). Both the ES cells and the iPS cells on type I collagen formed more compact spherical colonies than those of typical undifferentiated cells on MEF feeder layer. In contrast, the undifferentiated cells on fibronectin or gelatin formed less compact colonies (FIG. 1A). The cells on the E-cadherin substrata dispersed into single cells. In order to examine whether the adhesion mechanism of the ES cells and the iPS cells on the feeder-free artificial ECMs is integrin-independent, their integrin activity was measured. The phosphorylation state of FAK activated by culturing the cells on gelatin or E-cad-Fc was examined by Western blotting (FIG. 1B). On gelatin, the level of phosphorylation at Thy-397 of FAK was higher than that of the mES cells on the E-cad-Fc substrata. The phosphorylation level of FAK was slightly higher in the serum-containing media. This is presumably due to the presence of extracellular matrix molecules (such as fibronectin) in the FBS media. These results suggest that the initial adhesion of the ES cells on the E-cadherin substrata is not dependent on integrin. The faint bands of activated FAK in the lanes of the E-cadherin substrata are thought to be caused by the mechanical stress in stretching cells generated from adhesion to the E-cadherin. In addition, the adhesion efficiency of the iPS cells on the E-cadherin substrata was not affected even under serum-free conditions. This suggests that cadherin-based substrata can be suitably applied to spontaneous proliferation or differentiation under serum-free medium conditions (FIG. 1C).

From these results, it was thought that the ES cells and the iPS cells could exhibit a more excellent pluripotency on E-cadherin-based extracellular matrices. The morphology of the ES cell colonies and the iPS cell colonies whose alkaline phosphatase (AP) activity, which is widely used as an undifferentiation marker, is positive was observed. The proportion of the positive colonies was high in the cells cultured on type I collagen, but was low in the cells cultured on fibronectin or gelatin (FIG. 1D). Interestingly, the cells exhibiting single-cell-dispersing morphology on E-cadherin substrata had AP activity. The results of the flow cytometry of Nanog-GFP protein expression in miPS cells cultured for 4 days were similar to the results of the AP staining. The proportion of Nanog-GFP expressing cells was high in the cells on E-cadherin substrate (~77%) and on collagen (~71%), and was low the cells on gelatin (~67%) and on fibronectin (~54%) (FIG. 1E).

The results of immunochemical analysis of the expression of the stage-specific embryonic antigen 1 protein, which is used as an undifferentiated mES cell marker, were similar to the results of the AP staining and the Nanog expression in the cells on gelatin or E-cad-Fc substrata (FIG. 1F). The above data suggests that the undifferentiated state of feeder-dependent ES cells and iPS cells can be maintained on cadherin-based substrata for a long period of time. In addition, it was also shown that miPS cells maintained their pluripotency even after passaging on E-cad-Fc substrata. miPS cells on MEFs at passage 13 were cultured on E-cad-Fc substrata and maintained in the presence of an undifferentiating medium for 7 more passage. These iPS cells at passage 20 were induced to form embryoid bodies (EBs) by culturing the cells in the absence of LIF for 3 days in a form of hanging drops, and transferring the drops to culture dishes coated with gelatin. The cells on gelatin were cultured for additional 2 days, and the capability of these cells to spontaneously differentiate was confirmed using lineage-specific markers to examine their pluripotency. The iPS cell-derived EBs in the absence of LIF expressed an ectoderm marker (Sox1), mesendoderm markers (Goosecoid and Branchyury), endoderm markers (Sox17, Foxa2 and Gata6) and a mesoderm marker (Gata1), and the expression amount of an undifferentiated iPS cell marker (Oct3/4) were reduced (FIG. 1G). This result suggests that miPS cells can be maintained on E-cad-Fc without compromising their pluripotent capability to differentiate into all three germ layers.

<Expression of E-Cadherin and N-Cadherin in ES Cells and iPS Cells>

It has been reported that neural differentiation of mES cells is associated with the switching from E-cadherin to N-cadherin (Spencer H L et al., Mol. Biol. Cell: 2007; 18: 2838-51). In order to establish cadherin-based ECMs, the expression patterns of E-cadherin and N-cadherin during the differentiation of mES cells and miPS were evaluated. The evaluation was carried out by immunostaining of undifferentiated mES cells and miPS cells (FIG. 2A). In the majority of the cells, only E-cadherin was expressed on the cell surface. In contrast, no expression of N-cadherin was observed on the cell surface of the undifferentiated mES cells and miPS cells. P19 cell line which expresses E-cadherin and N-cadherin was used as a positive control. In order to observe the switching from E-cadherin to N-cadherin, neural differentiation was induced in the presence of DKK-1 and Lefty-A using the hanging drop method. Total E-cadherin protein and total N-cadherin protein were analyzed by Western blotting of whole cell lysates (FIG. 2B). N-cadherin protein was not observed in undifferentiated cells, but was detected from the cells on 4 days after the beginning of the differentiation induction, and the amount of N-cadherin protein was increased in the cells on 10 days after the beginning of the differentiation induction. In contrast, E-cadherin protein was detected in undifferentiated cells, but the expression amount thereof was substantially decreased in the presence of neural differentiation media. The E-cadherin expression and the N-cadherin expression were overlapped during the period from 4 to 6 days after the beginning of the culturing. Considering the E-cadherin function of adhesion of and the N-cadherin function of neural differentiation of undifferentiated mES cells or undifferentiated miPS cells, the present inventors arrived at the idea to attempt to induce homogeneous neural progenitors from mES cells or miPS cells by using two fusion proteins of cadherin superfamily proteins (E-cadherin, N-cadherin) individually or in combination.

<Substrata Co-Immobilized with E-Cadherin and N-Cadherin>

First, we investigated by using ELISA the optimized concentrations for immobilizing an E-cad-Fc fusion protein and an N-cad-Fc fusion protein onto polystyrene surface. Adsorption of the individual fusion proteins onto polystyrene surfaces was increased in a dose-dependent manner, reaching a monolayer concentration at 10 μg/ml. We also confirmed that the adsorption ratio of ES cells onto E-cad-Fc substrata was also dose-dependent, and found that E-cad-Fc substrata immobilized with 5 μg/ml E-cad-Fc provide a high adsorption ratio of ES cells (about 85%). Next, we investigated the monolayer concentration of a mixture of E-cad-Fc and N-cad-Fc with keeping the E-cad-Fc concentration fixed in 5 μg/ml. As a result, 5 μg/ml E-cad-Fc and 5 μg/ml N-cad-Fc were suitable for the co-immobilization of E-cad-Fc and N-cad-Fc (hereinafter also referred to as E-/N-cad-Fc) (FIG. 3A).

<Cell Adsorption onto and Growth on Co-Immobilized Substrata>

In order to confirm the efficacy of fusion protein-based (E-cad-Fc, N-cad-Fc) ECMs, the adsorption capabilities of ES cells and iPS cells in undifferentiating media or differentiation-inducing media onto the fusion protein-based ECMs were examined. The ES cells and the iPS cells adsorbed onto gelatin-coated surfaces, collagen-coated surfaces and 10 μg/ml E-cad-Fc-coated surfaces, and the adsorption efficiencies onto the three types of surfaces were similar to each other in the ES cells or the iPS cells (FIGS. 3B and C). However, during the differentiation, these cells detached from the surfaces (data not shown). On the other hand, the surfaces coated with N-cad-Fc did not support the adsorption of the undifferentiated cells (FIG. 3B). Differentiated neural cells in neurosphere were adsorbed onto the surfaces coated with N-cad-Fc, and neurite outgrowth was observed there (data not shown). The neurite outgrowth was confirmed through βIII-tubulin expression. Therefore, we used surfaces co-immobilized with E-cad-Fc and N-cad-Fc for culturing of mES cells and miPS cells and for differentiation thereof into neural lineages. We examined the adsorption capabilities of mES cells and miPS cells onto E-/N-cad-Fc co-immobilized substrata. The adsorption ratios of the ES cells or the iPS cells onto the E-/N-cad-Fc co-immobilized substrata were about 80% (FIGS. 3B and C), and all the cells exhibited single-cell-dispersing morphology (FIG. 3D). On surfaces coated with gelatin, both ES cells and iPS cells formed aggregated colonies. By using N-cadherin as the ECM in neural differentiation protocol, the effect of immobilized N-cadherin substratum on early stage of the neural differentiation was evaluated. The expression of undifferentiation-specific markers (Oct3/4 and E-cadherin) and neural differentiation-specific markers (N-cadherin and nestin) in ES cells and iPS cells was examined. Collagen I-coated substratum, which is a conventional extracellular matrix, was used as a control. In undifferentiated ES cells and undifferentiated iPS cells cultured on E-/N-cad-Fc co-immobilized substrata in the presence of LIF for 2 days for the differentiation induction, N-cadherin and nestin were not expressed. On the other hand, the pluripotency markers, Oct3/4, E-cadherin (FIGS. 4A and B) and Nanog (data not shown) were expressed in almost all the cells.

<Differentiation of ES Cells and iPS Cells into Neural Progenitor Cells>

Schematic representation of the neural differentiation induction using monolayer forming medium conditions is shown in FIG. 5A. We mainly focused on the generation of neurons, and, for this purpose, mES cells and miPS cells were cultured in the presence of neural differentiation media for 12 days. The viability and proliferative ability of these cells on E-/N-cad-Fc co-immobilized substrata in the presence of neural differentiation media were examined by MTT assay. From the growth curve of the mES cells (FIG. 5B) and the growth curve of the miPS cells (FIG. 5C), it was shown that their proliferative ability on E-/N-cad-Fc co-immobilized substrata were higher than that of the cells on culture dishes coated with gelatin, collagen or fibronectin. This result suggests that differentiated cells can be efficiently generated by using the artificial extracellular matrix. In addition, the exposure of mES cells and miPS cells to neural differentiation media induced prominent morphological changes of dispersed single mES (FIG. 5D) and miPS cells (data not shown) on E-/N-cad-Fc co-immobilized substrata. By using the cadherin-based ECMs, the homogeneity of cell populations could be maintained throughout all stages of differentiation, and generation of neurites was observed within 10 days after the beginning of differentiation induction. In order to confirm the progress of the neural differentiation, we examined differentiation stage-specific markers, including a primitive ectoderm marker, a primitive neural stem cell marker, a neural stem cell marker and a neural progenitor cell marker. Finally, we confirmed cells having phenotypic and genotypic characteristics of neurons or glial cells. mES cells and miPS cells which were expressing Nanog and Oct3/4 were induced into primitive ectoderms, and they expressed brain lipid binding protein (BLBP). The amount of mRNA transcript of Sox2 was elevated with the decrease of Nanog expression within 2 days after the beginning of the differentiation induction (FIG. 5E). The differentiated cells at this stage expressed low level of N-cadherin and neurogenin (Ngn1). These cells were then induced into primitive neural stem cells (NSCs) that express low levels of intermediate filament protein nestin and N-cadherin and exhibit spherical morphology within 4 days after the beginning of the differentiation induction (FIG. 6A and FIG. 6B). In the cells with primitive NSC-like morphology, the expression amounts of BLBP and Pax6 were increased, and the morphology was changed into spindle-like morphology reminiscent of the morphology of radial glial cells (FIG. 5D and FIG. 6C). BLBP expression was initially observed in many cells, but rapidly disappeared within 6 days after the beginning of the differentiation induction (FIG. 7A). Moreover, the expression amounts of N-cadherin, Ngn1 and Sox2 were increased compared to those of the primitive ectoderms. All these results suggest that the switching from ES cells (Oct3/4$^+$, Nanog$^+$, Sox2$^+$, Nestin$^-$, Ngn1$^-$) to neuroectoderm progenitor cells (N-cad$^+$, Nestin$^+$, Ngn1$^+$, BLBP$^-$) was completed within 6 days. For comparative study, time dependent analysis of nestin expression in mES cells (FIGS. 7B and 7C) and miPS cells (FIG. 7B and FIG. 7D) on gelatin substrata or E-/N-cad-Fc co-immobilized substrata was carried out. In the cells on E-/N-cad-Fc co-immobilized substrata, the amount of mRNA transcript of nestin was high throughout all stages of differentiation into neural progenitor cells, as compared to that of the cells on gelatin substrata. Moreover, in the results of immunofluorescent staining, the results of nestin expression and N-cadherin expression were similar to each other in cells on E-/N-cad-Fc co-immobilized substrata or cells on gelatin substrata. In contrast, an endoderm marker (hepatocyte nuclear factor; HNF4α) and a mesoderm marker (Gata1) were undetectable in the cells within 6 days after the beginning of the differentiation induction (data not shown). We monitored time-dependent decrease in the amount of Nanog expression in miPS cell-derived neural progenitor cells to examine whether selective differentiation into neural lineages was observed. In homogeneous cell populations on E-/N-cad-Fc co-immobilized substrata, Nanog expression was dramatically decreased. In differentiated miPS cells, Nanog expression became undetectable within 6 days (FIG. 7E). In contrast, in aggregated cells on gelatin substrata, Nanog expression was observed. This supports the findings, reported by Yin Q L et al., Nat. Biotechnol., 2003; 21(2): 183-6, that the loss of an undifferentiated ES cell marker is asynchronous within cell clusters and some cell clusters can escape induction of neural differentiation and maintain their undifferentiated state. Similar phenomenon was observed also in the case of culturing miPS cells on an E-/N-cad-Fc co-immobilized substratum to generate homogeneous populations. The expression of Nanog gene was prominent inside the compact cell aggregates, and this was clearly distinguishable from that in monolayer of non-aggregated cells exhibiting neural progenitor cell-like morphology. This indicates the advantage of the homogeneous culturing conditions that contamination of undifferentiated cells can be eliminated (FIG. 8).

<Neural Differentiation>

The mES cell-derived or miPS cell-derived neural progenitor cells were cultured in the presence of bFGF to induce cells having neural characteristics. The induction of the neural progenitor cells into neural cells was confirmed in two different ways. First, the cell morphology up to 12 days after the beginning of the differentiation induction was observed. Second, neural cell markers such as microtubule associated protein 2 (MAP2), tyrosine hydroxylase (TH), βIII-tubulin (Tuj), a glial cell marker (GFAP) were analyzed by RT-PCR. Cells with neuronal morphology began to appear within 8 days after the beginning of the differentiation induction and were prominent on 12 days (FIG. 5D). In order to examine whether neural progenitor cells undergo neuron-producing and later glia-producing progenitors, the production of neurons and glia throughout the monolayer differentiation inducing protocol was evaluated. As a result, the number of βIII-tubulin$^+$ neurons was increased up to day 12. On the other hand, GFAP expressing glial cells were undetectable. This corresponds to the notion that neurogenesis is an earlier event than gliogenesis (FIG. 9A). In addition, differentiation induction of mES cells and miPS cells under low density culturing conditions (explained in FIG. 8) was carried out. Both the mES cells and the miPS cells differentiated into βIII-tubulin-expressing neural cells having neurites shorter than those of the cells cultured under high density conditions (FIG. 9B). Within 10 days after the beginning of the differentiation induction, the amounts of MAP2, Pax6 and TH transcripts were high, and GFAP transcription was not observed. This indicates that neuronal subtypes predominated over glial cells (FIG. 9C). Compared to the cells on gelatin substrata, the cells on cadherin-based substrata exhibited longer neurite outgrowth. This supports that intercellular contact or cell clusters are not necessary for neurite outgrowth (Gavallaro U et al., Nat. Rev. Mol. Cell Biol., 2011; 12:189-97).

The invention claimed is:

1. A cell culture substrate, which is used for culturing for induction into neural progenitor cells or neural cells, characterized in that, onto the surface, at least two proteins are immobilized or coated, wherein said at least two proteins comprise: a first protein which is selected from the group consisting of a fusion protein comprising an entire or partial region of N-cadherin, and a fusion protein comprising an entire or partial region of a protein homologous to N-cadherin; and a second protein which is selected from the group consisting of a protein belonging to cadherin family other than N-cadherin, a fusion protein comprising at least one extracellular (EC) domain selected from EC1 domain, EC2 domain, EC3 domain, EC4 domain and EC5 domain of a protein belonging to cadherin family other than N-cadherin, and a fusion protein comprising at least one extracellular (EC) domain selected from EC1 domain, EC2 domain, EC3 domain, EC4 domain and EC5 domain of a protein homologous to a protein belonging to cadherin family other than N-cadherin, wherein said protein belonging to cadherin family other than N-Cadherin is E-cadherin wherein the concentration of the first protein is 3-1000 μg/mL and the concentration of the second protein is 0.01-1000 μg/mL; ac4 wherein the substrate comprises polystyrene, polyethylene or polypropylene; and wherein said protein homologous to N-cadherin is a protein which comprises one or more of the EC1 domain, EC2 domain, EC3 domain, EC4 domain and EC5 domain, and which has hemophilic binding ability with N-cadherin.

2. The cell culture substrate of claim 1, wherein a fusion protein comprising at least one extracellular (EC) domain selected from EC1 domain, EC2 domain, EC3 domain, EC4 domain and EC5 domain of E-cadherin or of a protein homologous to E-cadherin, and a fusion protein comprising an entire or partial region of N-cadherin or a protein homologous to N-cadherin are immobilized or coated onto the surface.

3. The cell culture substrate of claim 1, wherein said protein homologous to E-cadherin is a protein which comprises one or more of the EC1 domain, EC2 domain, EC3 domain, EC4 domain and EC5 domain, and which has homophilic binding ability with E-cadherin.

4. The cell culture substrate of claim 1, wherein the fusion protein comprising an entire or partial region of N-cadherin or a protein homologous to N-cadherin is a fusion protein of an entire or partial region of N-cadherin or a protein homologous to N-cadherin and an immunoglobulin Fc region.

5. The cell culture substrate of claim 1, wherein the fusion protein comprising at least one extracellular (EC) domain selected from EC1 domain, EC2 domain, EC3 domain, EC4 domain and EC5 domain of E-cadherin or of a protein homologous to E-cadherin is a fusion protein of at least one extracellular (EC) domain selected from EC1 domain, EC2 domain, EC3 domain, EC4 domain and EC5 domain of E-cadherin or of a protein homologous to E-cadherin and an immunoglobulin Fc region.

6. A cell culture substrate, characterized in that, onto the surface, two or more selected from the group consisting of a protein belonging to cadherin family and a fusion protein comprising an entire or partial region of a protein belonging to cadherin family are immobilized or coated.

7. A cell culturing method, characterized by growing pluripotent stem cells using the cell culture substrate of claim 1 and a liquid medium while maintaining their undifferentiated state and pluripotency.

8. A method for inducing differentiation of pluripotent stem cells, characterized by differentiating pluripotent stem cells using the cell culture substrate of claim 1 and a liquid medium containing a differentiation-inducing factor(s).

9. The method for inducing differentiation of pluripotent stem cells of claim 8, by which pluripotent stem cells are differentiated into neural progenitor cells or neural cell.

10. A method of producing neural progenitor cells or neural cells, characterized by culturing ES cells or iPS cells on the cell culture substrate of claim 1 using a liquid medium containing a differentiation-inducing factor(s).

11. The cell culture substrate of claim 1, wherein a fusion protein comprising at least one extracellular (EC) domain selected from EC1 domain, EC2 domain, EC3 domain, EC4 domain and EC5 domain of E-cadherin or of a protein homologous to E-cadherin, and a fusion protein comprising an entire or partial region of N-cadherin or a protein homologous to N-cadherin are immobilized or coated onto the surface.

12. The cell culture substrate of claim 2, wherein said protein homologous to N-cadherin is a protein which comprises one or more of the EC1 domain, EC2 domain, EC3 domain, EC4 domain and EC5 domain, and which has homophilic binding ability with N-cadherin.

13. The cell culture substrate of claim 2, wherein said protein homologous to E-cadherin is a protein which comprises one or more of the EC1 domain, EC2 domain, EC3 domain, EC4 domain and EC5 domain, and which has homophilic binding ability with E-cadherin.

14. The cell culture substrate of claim 1, wherein said protein homologous to E-cadherin is a protein which comprises one or more of the EC1 domain, EC2 domain, EC3 domain, EC4 domain and EC5 domain, and which has homophilic binding ability with E-cadherin.

15. The cell culture substrate of claim 1, wherein the first fusion protein and the second fusion protein are immobilized or coated onto the surface.

\* \* \* \* \*